US009044447B2

(12) United States Patent
Corey et al.

(10) Patent No.: US 9,044,447 B2
(45) Date of Patent: Jun. 2, 2015

(54) ANTIGENIC PEPTIDE OF HSV-2 AND METHODS FOR USING SAME

(75) Inventors: Lawrence Corey, Mercer Island, WA (US); Kerry J. Laing, Seattle, WA (US); Anna Wald, Seattle, WA (US); David M. Koelle, Seattle, WA (US)

(73) Assignees: UNIVERSITY OF WASHINGTON, Seattle, WA (US); FRED HUTCHISON CANCER RESEARCH CENTER, Seattle, WA (US)

( * ) Notice: Subject to any disclaimer, the term of this patent is extended or adjusted under 35 U.S.C. 154(b) by 119 days.

(21) Appl. No.: 13/262,833

(22) PCT Filed: Apr. 3, 2010

(86) PCT No.: PCT/US2010/029880
§ 371 (c)(1),
(2), (4) Date: Oct. 3, 2011

(87) PCT Pub. No.: WO2010/115172
PCT Pub. Date: Oct. 7, 2010

(65) Prior Publication Data
US 2012/0027789 A1 Feb. 2, 2012

Related U.S. Application Data

(60) Provisional application No. 61/166,637, filed on Apr. 3, 2009, provisional application No. 61/228,489, filed on Jul. 24, 2009.

(51) Int. Cl.
| A61K 39/245 | (2006.01) |
| A61K 9/19 | (2006.01) |
| C07K 14/005 | (2006.01) |
| A61K 39/00 | (2006.01) |
| C07K 7/08 | (2006.01) |
| A61K 9/00 | (2006.01) |

(52) U.S. Cl.
CPC .............. *A61K 39/245* (2013.01); *A61K 9/0019* (2013.01); *A61K 39/00* (2013.01); *A61K 2039/5158* (2013.01); *C07K 14/005* (2013.01); *C12N 2710/16622* (2013.01)

(58) Field of Classification Search
CPC ................ A61K 9/0019; A61K 39/00; A61K 2039/5158; A61K 39/245; A61K 38/00; C12N 2710/16622; C12N 2710/16634; C07K 14/005; C07K 5/00; C07K 14/035; C07K 16/08; C07K 7/06; C07K 7/08
See application file for complete search history.

(56) References Cited

U.S. PATENT DOCUMENTS

| 4,859,587 A | 8/1989 | Roizman |
| 5,384,122 A | 1/1995 | Cunningham et al. |
| 5,538,724 A | 7/1996 | Butcher |
| 5,632,992 A | 5/1997 | Nesburn et al. |
| 5,714,152 A | 2/1998 | Burke et al. |
| 5,747,039 A | 5/1998 | Burke et al. |
| 5,750,110 A | 5/1998 | Prieels et al. |
| 6,017,735 A | 1/2000 | O'Hare et al. |
| 6,200,577 B1 | 3/2001 | McLauchlan et al. |
| 6,340,577 B1 | 1/2002 | Hope et al. |
| 6,375,952 B1 | 4/2002 | Koelle |
| 6,413,518 B1 | 7/2002 | Koelle |
| 6,635,258 B2 | 10/2003 | Burke |
| 6,814,969 B2 | 11/2004 | Koelle |
| 6,821,519 B2 * | 11/2004 | Day et al. ................... 424/231.1 |
| 6,855,317 B2 | 2/2005 | Koelle |
| 6,962,709 B2 | 11/2005 | Koelle |
| 7,037,509 B2 | 5/2006 | Koelle |
| 7,078,041 B2 | 7/2006 | Koelle |
| 7,431,934 B2 | 10/2008 | Koelle |
| 7,666,434 B2 | 2/2010 | Koelle |
| 7,744,903 B2 | 6/2010 | Koelle |
| 8,067,010 B2 | 11/2011 | Koelle |
| 2002/0090610 A1 | 7/2002 | Hosken et al. |

(Continued)

FOREIGN PATENT DOCUMENTS

| AU | 782676 | 12/2005 |
| CA | 2336523 | 2/2000 |

(Continued)

OTHER PUBLICATIONS

Hosken N, McGowan P, Meier A, Koelle DM, Sleath P, Wagener F, Elliott M, Grabstein K, Posavad C, Corey L. Diversity of the CD8+ T-cell response to herpes simplex virus type 2 proteins among persons with genital herpes. J Virol. Jun. 2006;80(11):5509-15.*
Koelle DM, Liu Z, McClurkan CL, Cevallos RC, Vieira J, Hosken NA, Meseda CA, Snow DC, Wald A, Corey L. Immunodominance among herpes simplex virus-specific CD8 T cells expressing a tissue-specific homing receptor. Proc Natl Acad Sci U S A. Oct. 28, 2003;100(22):12899-904. Epub Oct. 17, 2003.*
Chentoufi AA, Zhang X, Lamberth K, Dasgupta G, Bettahi I, Nguyen A, Wu M, Zhu X, Mohebbi A, Buus S, Wechsler SL, Nesburn AB, BenMohamed L. HLA*A-0201-restricted CD8+ cytotoxic T lymphocyte epitopes identified from herpes simplex virus glycoprotein D. J Immunol. Jan. 1, 2008;180(1):426-37.*
Laing KJ, Magaret AS, Mueller DE, Zhao L, Johnston C, De Rosa SC, Koelle DM, Wald A, Corey L. Diversity in CD8(+) T cell function and epitope breadth among persons with genital herpes. J Clin Immunol. Sep. 2010;30(5):703-22. Epub Jul. 16, 2010.*

(Continued)

*Primary Examiner* — Benjamin P Blumel
*Assistant Examiner* — Rachel Gill
(74) *Attorney, Agent, or Firm* — Karen S. Canady; canady + lortz LLP

(57) ABSTRACT

The invention provides HSV antigens that are useful for the prevention and treatment of HSV infection, including epitopes confirmed to be recognized by T-cells derived from herpetic lesions. T-cells having specificity for antigens of the invention have demonstrated cytotoxic activity against cells loaded with virally-encoded peptide epitopes, and in many cases, against cells infected with HSV. The identification of immunogenic antigens responsible for T-cell specificity provides improved anti-viral therapeutic and prophylactic strategies. Compositions containing antigens or polynucleotides encoding antigens of the invention provide effectively targeted vaccines for prevention and treatment of HSV infection.

21 Claims, No Drawings

(56) References Cited

U.S. PATENT DOCUMENTS

| | | | |
|---|---|---|---|
| 2003/0165819 A1* | 9/2003 | McGowan et al. | 435/5 |
| 2003/0165820 A1* | 9/2003 | Day et al. | 435/5 |
| 2005/0130132 A1* | 6/2005 | Day et al. | 435/5 |
| 2005/0163794 A1* | 7/2005 | Koelle et al. | 424/186.1 |
| 2010/0215693 A1* | 8/2010 | Koelle et al. | 424/204.1 |
| 2011/0135687 A1 | 6/2011 | Koelle | |
| 2012/0027790 A1 | 2/2012 | Koelle | |
| 2012/0328655 A1* | 12/2012 | Dubensky et al. | 424/231.1 |

FOREIGN PATENT DOCUMENTS

| | | |
|---|---|---|
| CA | 2379623 | 4/2001 |
| CA | 2454750 | 2/2003 |
| CA | 2492598 | 1/2004 |
| EP | 1102790 | 5/2001 |
| EP | 1222281 | 11/2006 |
| EP | 2191845 | 6/2010 |
| EP | 1420821 | 11/2010 |
| EP | 2011510 | 1/2011 |
| EP | 2316479 | 5/2011 |
| JP | 4519461 | 8/2010 |
| NZ | 509974 | 2/2004 |
| NZ | 517959 | 9/2004 |
| WO | WO 92/02251 | 2/1992 |
| WO | WO 95/06055 | 3/1995 |
| WO | WO 95/16779 | 6/1995 |
| WO | WO 97/05265 | 2/1997 |
| WO | WO 98/04708 | 2/1998 |
| WO | WO 98/20016 | 5/1998 |
| WO | WO 98/55145 | 12/1998 |
| WO | WO 99/28478 | 6/1999 |
| WO | WO 99/47687 | 9/1999 |
| WO | WO 00/08051 | 2/2000 |
| WO | WO 01/23414 | 4/2001 |
| WO | WO 02/02131 | 1/2002 |
| WO | WO 03/086308 | 10/2003 |

OTHER PUBLICATIONS

Snyder A, Wisner TW, Johnson DC. Herpes simplex virus capsids are transported in neuronal axons without an envelope containing the viral glycoproteins. J Virol. Nov. 2006;80(22):11165-77. Epub Sep. 13, 2006.*

Chentoufi AA, Kritzer E, Yu DM, Nesburn AB, Benmohamed L. Towards a rational design of an asymptomatic clinical herpes vaccine: the old, the new, and the unknown. Clin Dev Immunol. 2012;2012:187585. Epub Mar. 26, 2012.*

Kim M, Taylor J, Sidney J, Mikloska Z, Bodsworth N, Lagios K, Dunckley H, Byth-Wilson K, Denis M, Finlayson R, Khanna R, Sette A, Cunningham AL. Immunodominant epitopes in herpes simplex virus type 2 glycoprotein D are recognized by CD4 lymphocytes from both HSV-1 and HSV-2 seropositive subjects. J Immunol. Nov. 1, 2008;181(9):6604-15.*

Zhang X, Chentoufi AA, Dasgupta G, Nesburn AB, Wu M, Zhu X, Carpenter D, Wechsler SL, You S, BenMohamed L. A genital tract peptide epitope vaccine targeting TLR-2 efficiently induces local and systemic CD8+ T cells and protects against herpes simplex virus type 2 challenge. Mucosal Immunol. Mar. 2009;2(2):129-43. Epub Dec. 24, 2008.*

Laing KJ, Dong L, Sidney J, Sette A, Koelle DM. Immunology in the Clinic Review Series; focus on host responses: T cell responses to herpes simplex viruses. Clin Exp Immunol. Jan. 2012;167(1):47-58.*

Zhu J, Hladik F, Woodward A, Klock A, Peng T, Johnston C, Remington M, Magaret A, Koelle DM, Wald A, Corey L. Persistence of HIV-1 receptor-positive cells after HSV-2 reactivation is a potential mechanism for increased HIV-1 acquisition. Nat Med. Aug. 2009;15(8):886-92. doi: 10.1038/nm.2006. Epub Aug. 2, 2009.*

Martin ET, Koelle DM, Byrd B, Huang ML, Vieira J, Corey L, Wald A. Sequence-based methods for identifying epidemiologically linked herpes simplex virus type 2 strains. J Clin Microbiol. Jul. 2006;44(7):2541-6.*

Bowie JU, Reidhaar-Olson JF, Lim WA, Sauer RT. Deciphering the message in protein sequences: tolerance to amino acid substitutions. Science. Mar. 16, 1990;247(4948):1306-10.*

Bui HH, Sidney J, Dinh K, Southwood S, Newman MJ, Sette A. Predicting population coverage of T-cell epitope-based diagnostics and vaccines. BMC Bioinformatics. Mar. 17, 2006;7:153.*

Stapler D, Lee ED, Selvaraj SA, Evans AG, Kean LS, Speck SH, Larsen CP, Gangappa S. Expansion of effector memory TCR Vbeta4+ CD8+ T cells is associated with latent infection-mediated resistance to transplantation tolerance. J Immunol. Mar. 1, 2008;180(5):3190-200.*

Aurelian et al., "Amino-terminal Epitope of Herpes Simplex Virus Type 2 ICP10 Protein as a Molecular Diagnostic Marker for Cervical . . . Neoplasia," Cancer Cells, 1989, 7: 187-191.

Bras, F. et al., "The left border of the genomic inversion of *Pseudorabies virus* contains genes homologous to the UL46 . . . gene," 1999, 60(1): 29-40.

Bjornberg, O. et al., "dUTIPhase from Herpes Simplex Virus Type 1; Purification from infected Green Monkey Kidney . . . Strain," Protein Expression and Purification, 1993, 4:149-159.

Carter, K.L. et al., "Alternatively spliced mRNAs predicted to yield frame-shift proteins and stable intron 1 RNAs of the herpes . . . cells", 1996, Proc. Natl. Acad. Sci., 93(22):12535-40.

Cox, et al., "Adjuvants—a classification and review of their modes of action," Vaccine, 1997, 15(3):248-256.

Dargan, D.J., "The effect of herpes simplex virus type 1 L-particles on . . . DNA," 1997, Virology, 239(2): 378-88.

De Plaen, E., "Cloning of Genes Coding for Antigens Recognized by Cytolytic T Lymphocytes," Immunology Methods Manual, 1997, 692-718.

Dolan, A., The Genome Sequence of Herpes Simplex Virus Type 2, Journal of Virology, 1998, 72(3):2010-2021.

Elliot, G. et al., Intercellular Trafficking and Protein Delivery by a Herpesvirus Structural Protein, Cell, 1997, 88:223-233.

Ettinger, et al., A Peptide Binding Motif for HLA-DQA1*0102/DQBI*0602, the Class II MHC . . . Mellitus, 1998, Journal of Immunology, 60(5):2365-2373.

Everett et al., "A Truncated Form of Herpes Simplex Virus Type 1 Immediate-Early Protein Vmw110 is Expressed in a Cell Type Dependent Manner," Virol., 1993, 197: 751-756.

Everett et al., "High level expression and purification of herpes simplex virus type 1 immediate early polypeptide Vmw110 ," J. Nucleic Acids Research, 1991, 19(22):6155-6161.

Fuhlbrigge, Robert C. et al., "Cutaneous lymphocyte antigen is a specialized form of PSGL-1 expressed on skin-homing T cells", Nature, Oct. 30, 1997, vol. 389, pp. 978-981.

Homey, B., "CCL27-CCRIO Interactions Regulate T Cell-mediated Skin Inflammation", Nature Medicine, Feb. 1992, 8(2).

Kawaguchi et al., "Herpes Simplex Virus 1 α Regulatory Protein ICPO Interacts with and Stabilizes the Cell Cycle Regulator Cyclin D3," J. Virol., 1997, 71(10): 7328-7336.

Khan, Naeem et al., "Comparative Analysis of CD8+ T Cell Responses against Human . . . Phenotype", J. of Infectious Diseases, Mar. 2002, vol. 185, pp. 1025-1034.

Koelle, D.M., "CD4 T-Cell Responses to Herpes Simplex virus Type 2 Major Capsid Portein VPF: Comparison . . . Glycoproteins," J of Virology, Dec. 2000, 74(23):11422-11425.

Koelle, D.M., "CD8 CTL from Genital Herpes Simplex Lesions; Recognition of Viral Tegument . . . Cells", Journal of Immunology, Mar. 2001, 166(6):4049-4058.

Koelle, D.M., "Expression of Cutaneous Lymphocyte-associated Antigen by CD8(+) T Cells Specific for a Skin-trophic Virus", Journal of Clinical Investigation, Aug. 2002, 110(4):537-548.

Koelle, D.M., "Recognition of Herpes Simplex Virus Type 2 Tegument Proteins by CD4 T Cells . . . " J.of Virology, 1998, 72(9): 7476-7483.

Koelle, D.M., "The Roles of T Lymphocytes in Host Responses to Herpes Simplex Virus," Herpes, 1995, 2:83-88.

Koelle, D.M., "Clearance of HSV-2 from Recurrent Genital Lesions Correlates with Infiltration of HSV-Specific Cytotoxic T Lymphoctyes," J of Clinical Investigation, 1998, 101(7):1500-1508.

(56) References Cited

OTHER PUBLICATIONS

Koelle, D.M., "Preferential Presentation of Herpes Simplex Virus T-Cell Antigen by HLA DQA1*0501/DQB1*0201 in Comparison to HLA DQA1*0201/DQB1*0201," Human Immunology, 1997, 53(2):195-205.

Koelle, D.M., "Direct Recovery of Herpes Simplex Virus (HSV)-Specific T Lymphocyte Clones from Recurrent Genital HSV-2 Lesions," The Journal of Infectious Diseases, 1994, 169:956-61.

Koelle, D.M., "Antigenic Specificities of Human CD+ T-Cell Clones Recovered from Recurrent Genital Herpes Simples Virus Type 2 Lesions," Journal of Virology, 1994, 68(5):2803-2810.

Koelle, D.M., "Tegument-specific, virus-reactive CD4 T cells localize to the cornea in herpes . . . humans," 2000, J. of Virology, 74(23):10930-10938.

Kwok, W.W., "Peptide Binding Affinity and pH Variation Establish Functional Thresholds for Activation of HLA-DQ-Restricted T Cell Recognition," Human Immunology, 1999, 60(7):619-626.

Leib et al., "Immediate-Early Regulatory Gene Mutants Define Different Stages in the Establishment . . . Latency," J. Virology, 1989, 63(2):759-768.

Manickan, E. et al., Vaccination with recombinant vacccinia viruses expressing ICP27 induces protective . . . cells,: J. Virol, 1995, 69(8):4711-4716.

Marshall, Natalie A., "Rapid reconstitution of Epstein-Barr virus-specific T lymphocytes . . . transplantation", Immunology, Oct. 15, 2000, Blood, 96(8): 2814-2821.

McGeoch, D.J. et al., "HSV2 ICP0 protein," 1991, Swissprot, XP002161838.

McGeoch, D.J. et al., "The complete DNA sequence of the long unique region in the genome of herpes . . . 1," 1988, of General Virology, 69: 1531-1574.

McGeoch, D.J. et al., "Major capsid Protein," Database EMBL [Online] E.B.I. Hinxton U.K., May 1, 1997, 2pages.

McGeoch, D.J. et al., "Comparative sequence analysis of the long repeat regions and adjoining parts of the long unique . . . 2", Journal of General Virology, 1991, 72(12): 3057-3075.

NCBI Entrez, locus CAA32299 tegument protein (*Human herpesvirus1*) [online] [retrieved Feb. 27, 2004].

NCBI Entrez, locus CAB06735 tegument protein (*Human herpesvirus2*) [online] [retrieved Feb. 27, 2004].

Newcomb, W.W. et al., "Cell-Free Assembly of the Herpes Simplex Virus Capsid," J. of Virology, The American Society for Microbiology, 1994, 68(9):6059-6063.

Nozawa, Naoki, "Identification and Characterization of the UL7 Gene Product of Herpes Simplex Virus Type 2", Virus Genes, Jun. 2002, 24(3):257-266.

Paoletti, "Applications of Pox Virus Vectors to Vaccination: An Update," Proceedings of the National Academy of Science USA, Oct. 1996, 93:11349-11353.

Pober, Jordan S. et al., "Human Endothelial Cell Presentation of Antigen and the Homing of Memory/Effector T Cells to Skin", Annals New York Academy of Sciences, 2001, vol. 941, pp. 12-25.

Posavad, C.M., "High Frequency of CD8+ Cytotoxic T-Lymphoctye Precursors Specific for Herpes Simplex Viruses in Persons with Genital Herpes," J of Virology, 1996, 70(11):8165-8168.

Reichstetter, S., "MCH-Peptide Ligand Interactions Establish a Functional Threshold for Antigen-Specific T Cell Recognition," Human Immunology, 1999, 60(7):608-618.

Roizman, B. et al., "Herpes Simplex Viruses and Their Replication", Fundamental Virology, 2nd Edition, ed. Fields et al, Raven Press, 1991, New York, pp. 849-895.

Roux et al., "Mutation of isoleucine 747 by a threonine alters the ligand responsiveness of the human glucocorticoid receptor," Molecular Endocrinology, 1996, 10: 1214-1226.

Rueda et al., "Loss of Conserved Cysteine Residues in the Attachment (G) Glycoprotein of Two Human Respiratory Syncytial . . . (Hypermutations)," Virology, 1994, 198(2): 653-662.

Spencer et al., "Structure of the Herpes Simplex Virus Capsid: Peptide A862-H880 of the Major Capsid Protein Iss Displayed on the . . . Protrusions," Virology, Feb. 1997, 228(2):229-235.

Stanberry, "Glycoprotein-D-Adjuvant Vaccine to Prevent Genital Herpes," N. Engl. J. Med., 2002, 347(21):1652-1661.

Stanberry, Lawrence R., "Prospects for Control of Herpes Simplex Virus Disease through Immunization", Clinical Infectious Diseases, Mar. 2000, vol. 30, pp. 549-566.

Tatman, J.D. et al., "Assembly of Herpes Simplex Virus Type 1 Using a Panel of Recombinant Baculoviruses," J. of General Virology, 1994, 75: 1101-1113.

Tigges, M.A., "Human CD8+ Herpes Simplex Virus-Specific Cytotoxic T-Lymphocyte Clones Recognize Diverse Virion Protein Antigens," Journal of Virology, 1992, 66(3):1622-1634.

Williams, "Characterization of a Herpes Simplex Virus Type 2 Deoxyuridine . . . " Virology, 1987, 156:282-292.

Williams, "Deoxyuridine Triphosphate Nucleotidohydrolase Induced by Herpes Simplex Virus Type 1," Jnl. of Biological Chemistry, 1984, 259(16): 10080-10084.

Yanagida, N. et al., "Nucleotide and predicted amino acid sequences of Marek's disease virus homologues . . . proteins," 1993, vol. 74, Pt 9, pp. 1837-1845.

Yao et al., "Physical Interaction between the Herpes Simplex Virus Type 1 Immediate-Early Regulatory Proteins ICP0 and ICP4," J. Virol., 1994, 68(12):8158-8168.

Response filed in the EPO on Nov. 1, 2011 in response to an Office action dated Apr. 27, 2011 in corresponding EP App No. 99940918 (publication No. 1102790 / May 30, 2001).

* cited by examiner

ANTIGENIC PEPTIDE OF HSV-2 AND METHODS FOR USING SAME

This application claims the benefit of U.S. provisional patent applications 61/166,637, filed Apr. 3, 2009, and 61/228,489, filed Jul. 24, 2009, the entire contents of each of which is incorporated herein by reference.

STATEMENT REGARDING FEDERALLY SPONSORED RESEARCH

This invention was made with government support under grant number AI042528-11 awarded by the National Institutes of Health. The government has certain rights in the invention.

TECHNICAL FIELD OF THE INVENTION

The invention relates to molecules, compositions and methods that can be used for the treatment and prevention of viral infection and other diseases. More particularly, the invention identifies epitopes of herpes simplex virus type 2 (HSV-2) proteins that can be used for methods involving molecules and compositions having the antigenic specificity of HSV-specific T cells. In addition, the invention relates to methods for detecting, treating and preventing HSV infection, as well as methods for inducing an immune response to HSV. The epitopes described herein are also useful in the development of diagnostic and therapeutic agents for detecting, preventing and treating viral infection and other diseases.

BACKGROUND OF THE INVENTION

HSV-2 infects about 22% of persons in the US. The level of infection is increasing. HSV-2 infection is associated with an increased risk of acquisition of HIV-1 infection, the main cause of AIDS. HSV-2 infection is associated with death or morbidity of infants who are infected in the neonatal period by transit through areas of HSV-2 infection in the cervix or vagina. HSV-2 also causes painful recurrent ulcerations in the genital or rectal areas of some infected persons and as such leads to a very high level of health care utilization and pharmacy costs. There are positive data from a phase III clinical trial showing about 40% efficacy to prevent HSV-2 infection, and about 70% efficacy to prevent HSV-2-induced clinical disease (Stanberry, 2002, N. Engl. J. Med. 347(21):1652-1661. However there was only positive efficacy data in the subset of study participants who were female and who were uninfected with HSV type 1 at the time the study started. A very large phase III confirmatory clinical trial in HSV-1 uninfected women only is currently being planned and will take several years.

Once HSV-2 infection occurs, the virus causes latent infection of the sensory neurons in the ganglia that enervate the area of skin or mucosal infection. Periodically, the virus reactivates from latency in the neurons, travels down their axons, and causes a productive infection of the skin or mucosa in the areas that are enervated by the neuron. Current therapy can decrease this lytic replication in the skin or mucosa. However, current therapy does not remove latent virus from neurons. If the antiviral therapy is not being taken at the time the virus reactivates in the neuron, it will not prevent replication of the virus in the skin or mucosa, and thus is not able to reduce new symptoms or block the chance of shedding of live HSV-2 into the environment and thus transmission of HSV-2. Current therapy can be taken on a continual basis (suppressive therapy), which reduces symptomatic outbreaks and HSV-2 shedding, but as soon as it is stopped, the same underlying pattern of recurrent symptoms and lesions returns.

There remains a need to identify specific epitopes capable of eliciting an effective immune response to HSV infection. Such information can lead to the identification of more effective immunogenic antigens useful for the prevention and treatment of HSV infection.

SUMMARY OF THE INVENTION

The invention provides a number of specific epitopes encoded by the HSV genome that elicits an immune response in human subjects, including some for a large proportion of the human population, those persons with the common HLA allele A*02. The invention provides a specific epitope encoded by the HSV genome that elicits an immune response in those persons with the common HLA allele A*0201. The epitope is located in amino acids 369-383 of $U_L25$, and, more specifically, the 9 mer at amino acids 372-380 (FLWEDQTLL; SEQ ID NO: 1). The invention provides antigens containing one or more of these epitopes, polypeptides comprising antigens, polynucleotides encoding the polypeptides, vectors, and recombinant viruses containing the polynucleotides, antigen-presenting cells (APCs) presenting the polypeptides, immune cells directed against the epitopes, and pharmaceutical compositions. The pharmaceutical compositions can be used both prophylactically and therapeutically.

The invention additionally provides methods, including methods for preventing and treating infection, for killing infected cells, for inhibiting viral replication, for enhancing secretion of antiviral and/or immunomodulatory lymphokines, and for enhancing production of HSV-specific antibody. The method comprises administering to a subject an effective amount of a polypeptide, polynucleotide, recombinant virus, APC, immune cell or composition of the invention. The methods for killing infected cells and for inhibiting viral replication comprise contacting an infected cell with an immune cell of the invention. The immune cell of the invention is one that has been stimulated by an antigen of the invention or by an APC that presents an antigen of the invention. A method for producing such immune cells is also provided by the invention. The method comprises contacting an immune cell with an APC, preferably a dendritic cell, that has been modified to present an antigen of the invention. In a preferred embodiment, the immune cell is a T cell such as a CD4+ or CD8+ T cell.

The invention additionally provides pharmaceutical compositions comprising the antigens and epitopes identified herein. Also provided is an isolated polynucleotide that encodes a polypeptide of the invention, and a composition comprising the polynucleotide. The invention additionally provides a recombinant virus genetically modified to express a polynucleotide of the invention, and a composition comprising the recombinant virus. In one embodiment, the recombinant virus is a vaccinia virus, canary pox virus, HSV, lentivirus, retrovirus or adenovirus. A composition of the invention can be a pharmaceutical composition. The composition can optionally comprise a pharmaceutically acceptable carrier and/or an adjuvant.

DETAILED DESCRIPTION OF THE INVENTION

The invention provides HSV antigens that are useful for the prevention and treatment of HSV infection, and more particularly, a specific epitope encoded by the HSV genome that elicits an immune response in a large proportion of the human population. Disclosed herein are antigens and/or their constituent epitopes confirmed to be recognized by T-cells derived from herpetic lesions of infected patients having a known history and shedding levels. In some embodiments, T-cells having specificity for antigens of the invention have demonstrated cytotoxic activity against virally infected cells. The identification of immunogenic antigens responsible for T-cell specificity facilitates the development of improved anti-viral therapeutic and prophylactic strategies. Compositions containing antigens or polynucleotides encoding antigens of the invention provide effectively targeted vaccines for prevention and treatment of HSV infection.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids, and can be at least about 15 amino acids. Typically, optimal immunological potency is obtained with lengths of 8-10 amino acids. Those skilled in the art also recognize that additional adjacent sequence from the original (native) protein can be included, and is often desired, in an immunologically effective polypeptide suitable for use as a vaccine. This adjacent sequence can be from 1, 2, 3, 4, 5, 6, 7, 8, 9 or 10 amino acids in length to as much as 15, 20, 25, 30, 35, 40, 45, 50, 75 or 100 amino acids in length or more.

As used herein, particularly in the context of polypeptides of the invention, "consisting essentially of" means the polypeptide consists of the recited amino acid sequence and, optionally, adjacent amino acid sequence. The adjacent sequence typically consists of additional, adjacent amino acid sequence found in the full length antigen, but variations from the native antigen can be tolerated in this adjacent sequence while still providing an immunologically active polypeptide.

As used herein, "epitope" refers to a molecular region of an antigen capable of eliciting an immune response and of being specifically recognized by the specific immune T-cell produced by such a response. Another term for "epitope" is "determinant" or "antigenic determinant". Those skilled in the art often use the terms epitope and antigen interchangeably in the context of referring to the determinant against which an immune response is directed.

As used herein, "HSV polypeptide" includes HSV-1 and HSV-2, unless otherwise indicated. References to amino acids of HSV proteins or polypeptides are based on the genomic sequence information regarding HSV-2 as described in A. Dolan et al., 1998, J. Virol. 72(3):2010-2021.

As used herein, "substitutional variant" refers to a molecule having one or more amino acid substitutions or deletions in the indicated amino acid sequence, yet retaining the ability to be "immunologically active", or specifically recognized by an immune cell. The amino acid sequence of a substitutional variant is preferably at least 80% identical to the native amino acid sequence, or more preferably, at least 90% identical to the native amino acid sequence. Typically, the substitution is a conservative substitution.

One method for determining whether a molecule is "immunologically active", "immunologically effective", or can be specifically recognized by an immune cell, is the cytotoxicity assay described in D. M. Koelle et al., 1997, Human Immunol. 53:195-205. Other methods for determining whether a molecule can be specifically recognized by an immune cell are described in the examples provided hereinbelow, including the ability to stimulate secretion of interferon-gamma or the ability to lyse cells presenting the molecule. An immune cell will specifically recognize a molecule when, for example, stimulation with the molecule results in secretion of greater interferon-gamma than stimulation with control molecules. For example, the molecule may stimulate greater than 5 pg/ml, or preferably greater than 10 pg/ml, interferon-gamma secretion, whereas a control molecule will stimulate less than 5 pg/ml interferon-gamma.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "adjuvant" includes those adjuvants commonly used in the art to facilitate the stimulation of an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

As used herein, to "prevent" or "protect against" a condition or disease means to hinder, reduce or delay the onset or progression of the condition or disease.

Overview

HSV-2 encodes about 85 proteins using DNA which contains about 85 genes. Very little is known about which genes encode proteins that are recognized by HSV-2-specific CD8 T-cells. Each unique clonotype of CD8 T-cell recognizes an 8 to 10 amino acid linear fragment of a protein encoded by HSV-2. Most of these fragments, called epitopes, are 9 amino acids long, but there is no strict upper limit on their length. Each epitope is physically bound to a molecule on the surface of a cell (termed the antigen presenting cells). Typically, the antigen presenting cell is infected with HSV-2, although this is not always the case. In some instances, the antigen presenting cell may phagocytose material from outside the cell that contains non-viable HSV-2 material.

The HLA molecule, in the case of CD8 T-cell recognition, is a heterodimer composed of a HLA class I heavy chain molecule and the molecule β2 microglobulin. Because there are many different allelic variants of HLA class I molecules in the human population, an HSV-2 epitope peptide that binds to one allelic variant of HLA class I may not bind to another allelic variant. As a consequence, a HSV-2 epitope peptide that is recognized by CD8 T-cells from one person may not be recognized by CD8 T-cells from another person.

An HSV-2 antigen which has been proven to contain at least one smaller peptide epitope may contain diverse epitopes that are capable of being recognized by CD8 T-cells from many different persons. This pattern has generally been noted for the human immune response to many viruses. The invention described herein relates to the identity of HSV-2 protein antigens encoded by HSV-2 genes, and peptide epitopes that are internal fragments of these HSV-2 proteins. These HSV-2 proteins are logical vaccine compounds because they are now proven to stimulate T-cell responses.

HSV Polypeptides

In one embodiment, the invention provides an isolated herpes simplex virus (HSV) polypeptide. The polypeptide comprises an HSV protein described herein or a fragment thereof. In one embodiment, the fragment comprises a 15 mer listed in Table 1 of Example 1 below, or a substitutional variant thereof. In one embodiment, the fragment comprises amino acids 372 to 380 (FLWEDQTLL; SEQ ID NO: 1) of UL25 or a substitutional variant thereof. The reference to amino acid residues is made with respect to the proteins of the HSV-2 genome as described in A. Dolan et al., 1998, J. Virol. 72(3):2010-2021. The amino acid sequence of UL25 is as follows.

```
UL25 (SEQ ID NO: 2):
  1 mdpyypfdal dvwehrrfiv adsrsfitpe fprdfwmlpv fnipretaae raavlqaqrt 61 aaaaalenaa lqaaelpvdi errirpieqq vhhiadalea letaaaaaee adaardaear 121 gegaadgaap sptagpaaae mevqivrndp plrydtnlpv dllhmvyagr gaagssgvvf 181 gtwyrtiqer tiadfplttr sadfrdgrms ktfmtalvls lqscgrlyvg qrhysafeca 241 vlclyllyrt thesspdrdr apvafgdlla rlprylarla avigdesgrp qyryrddklp 301 kaqfaaaggr yehgalathv viativrhgv lpaapgdvpr dtstrvnpdd vahrddvnra 361 aaaflarghn lflwedqtll ratantital avlrrllang nvyadrldnr lqlgmlipga 421 vpaeaiarga sgldsgaiks gdnnlealcv nyvlplyqad ptveltqlfp glaalcldaq 481 agrplastrr vvdmssgarq aalvrltale linrtrtntt pvgeiinand algiqyeqgp 541 gllaqqarig lasntkrfat fnvgsdydll yflclgfipq ylsva
```

And for HSV-1, UL25 (SEQ ID NO: 3), the 15 mer corresponding to HSV-2 amino acids 369-383 is found at amino acids 364-378 (underlined) while the 9 mer corresponding to HSV-2 amino acids 372-380 is at amino acids 367-375 (per Genbank Accession No. ACM62247.1):

```
MDPYCPFDALDVWEHRRFIVADSRNFITPEFPRDFWMSPVFNLPRETAAEQVVVLQAQRTAAAAALENAA

MQAAELPVDIERRLRPIERNVHEIAGALEALETAAAAAEEADAARGDEPAGGGDGGAPPGLAVAEMEVQI

VRNDPPLRYDTNLPVDLLHMVYAGRGATGSSGVVFGTWYRTIQDRTITDFPLTTRSADFRDGRMSKTFMT

ALVLSLQACGRLYVGQRRYSAFECAVLCLYLLYRNTHGAADDSDRAPVTFGDLLGRLPRYLACLAAVIGT

EGGRPQYRYRDDKLPKTQFAAGGGRYEHGALASHIVIATLMHHGVLPAAPGDVPRDASTHVNPDGVAHHD

DINRAAAAFLSRGHNLFLWEDQTLLRATANTITALGVIQRLLANGNVYADRLNNRLQLGMLIPGAVPSEA

IARGASGSDSGAIKSGDNNLEALCANYVLPLYRADPAVELTQLFPGLAALCLDAQAGRPVGSTRRVVDMS

SGARQAALVRLTALELINRTRTNPTPVGEVIHAHDALAIQYEQGLGLLAQQARIGLGSNTKRFSAFNVSS

DYDMLYFLCLGFIPQYLSAV

UL19 (SEQ ID NO: 6):
MAAPARDPPGYRYAAAILPTGSILSTIEVASHRRLFDFFAAVRSDENSLYDVEFDALLGSYCNTLSLVRFLELGLS

VACVCTKFPELAYMNEGRVQFEVHQPLIARDGPHPVEQPVHNYMTKVIDRRALNAAFSLATEAIALLTGEALDGTG

ISLHRQLRAIQQLARNVQAVLGAFERGTADQMLHVLLEKAPPLALLLPMQRYLDNGRLATRVARAT

LVAELKRSFCDTSFFLGKAGHRREAIEAWLVDLTTATQPSVAVPRLTHADTRGRPVDG

VIVTTAAIKQRLLQSFLKVEDTEADVPVTYGEMVLNGANLVTALVMGKAVRSLDDVGR

HLLDMQEEQLEANRETLDELESAPQTTRVRADLVAIGDRLVFLEALERRIYAATNVPY

PLVGAMDLTFVLPLGLFNPAMERFAAHAGDLVPAPGHPEPRAFPPRQLFFWGKDHQVL

RLSMENAVGTVCHPSLMNIDAAVGGVNHDPVEAANPYGAYVAARAGPGADMQQRFLNA

WRQRLAHGRVRWVAECQMTAEQFMQPDNANLALELHPAFDFFAGVADVELPGGEVPPA

GPGAIQATWRVVNGNLPLALCPVAFRDARGLELGVGRHAMAPATIAAVRGAFEDRSYP

AVFYLLQAAIHGNEHVFCALARLVTQCITSYWNNTRCAAFVNDYSLVSYIVTYLGGDL

PEECMAVYRDLVAHVEALAQLVDDFTLPGPELGGQAQAELNHLMRDPALLPPLVWDCD

GLMRHAALDRHRDCRIDAGGHEPVYAAACNVATADFNRNDGRLLHNTQARAADAADDR

PHRPADWTVHHKIYYYVLVPAFSRGRCCTAGVRFDRVYATLQNMVVPEIAPGEECPSD

PVTDPAHPLHPANLVANTVKRMFHNGRVVVDGPAMLTLQVIAHNMAERTTALLCSAAP

DAGANTASTANMRIFDGALHAGVLLMAPQHLDHTIQNGEYFYVLPVHALFAGADHVAN

APNFPPALRDLARDVPLVPPALGANYFSSIRQPVVQHARESAAGENALTYALMAGYFK

MSPVALYHQLKTGLHPGFGFTVVRQDRFVTENVLFSERASEAYFLGQLQVARHETGGG

VNFTLTQPRGNVDLGVGYTAVAATGTVRNPVTDMGNLPQNFYLGRGAPPLLDNAAAVY

LRNAVVAGNRLGPAQPLPVFGCAQVPRRAGMDHGQDAVCEFIATPVATDINYFRRPCN

PRGRAAGGVYAGDKEGDVIALMYDHGQSDPARPFAATANPWASQRFSYGDLLYNGAYH

LNGASPVLSPCFKFFTAADITAKHRCLERLIVETGSAVSTATAASDVQFKRPPGCREL

VEDPCGLFQEAYPITCASDPALLRSARDGEAHARETHFTQYLIYDASPLKGLSL

UL46 (VP11/12; SEQ ID NO: 7):
  1 mqrrargass lrlarcltpa nlirganagv perrifagcl lptpegllsa avgvlrqrad 61 dlqpafltga drsvrlaarh hntvpesliv dglasdphyd yirhyasaak qalgevelsg 121 gqlsrailaq ywkylqtvvp sgldipddpa gdcdpslhvl lrptllpkll vrapfksgaa 181 aakyaaavag lrdaahrlqq ymffmrpadp srpstdtalr lsellayvsv lyhwaswmlw
```

```
241 tadkyvcrrl gpadrrfval sgsleapaet farhldrgps gttgsmqcma lraaysdvlg 301 hltrlahlwe tgkrsggtyg ivdaivstve vlsivhhhaq yiinatltgy vvwasdslnn 361 eyltaavdsq erfcrtaapl fptmtapswa rmelsikswf gaalapdllr sgtpsphyes 421 ilrlaasgpp ggrgavggsc rdkiqrtrrd nappplprar phstpaaprr crrhredlpe 481 pphvdaadrg pepcagrpat yythmagapp rlpprnpapp eqrpaaaarp laaqreaagv 541 ydavrtwgpd aeaepdqmen tyllpdddaa mpagvglgat paadttaaaa wpaeshapra 601 psedadsiye svgedggrvy eeipwvrvye nicprrrlag gaalpgdapd spyieaenpl 661 ydwggsalfs prratrapdp glslspmpar prtnalandg ptnvaalsal ltklkrgrhq 721 sh
UL49 (SEQ ID NO: 8):
  1 mtsrrsvksc preaprgthe elyygpvspa dpesprddfr rgagpmrarp rgevrflhyd 61 eagyalyrds ssddddesrdt arprrsasva gshgpgpara ppppggpvga ggrshappar 121 tpkmtrgapk asatpatdpa rgrrpaqads avlldapapt asgrtktpaq glakklhfst 181 appsptapwt prvagfnkry fcaavgrlaa tharlaavql wdmsrphtde dlnelldltt 241 irvtvcegkn llqranelvn pdaaqdvdat aaargrpagr aaatarapar sasrprrple
ICP0 (SEQ ID NO: 9):
  1 meprpgtssr adpgperppr qtpgtqpaap hawgmlndmq wlassdseee tevgisdddl 61 hrdstseags tdtemfeagl mdaatpparp paerqgsptp adaqgscggg pvgeeeaeag 121 gggdvcavct deiapplrcq sfpclhpfci pcmktwiplr ntcplcntpv aylivgvtas 181 gsfstipivn dprtrveaea avragtavdf iwtgnprtap rslslgghtv ralspttpwp 241 gtddedddla dvdyvppapr raprrgggga gatrgtsqpa atrpappgap rssssggapl 301 ragvgsgsgg gpavaavvpr vaslppaagg gragarrvge daaaaegrtp parqpraaqe 361 ppivisdspp psprrpagpg plsfvssssa qvssgpgggg lpqssgraar praavaprvr 421 sppraaaapv vsasadaagp appavpvdah raprsrmtqa qtdtqaqslg ragatdargs 481 ggpgaeggpg vprgtntpga aphaaegaaa rprkrrgsds gpaasssass saaprsplap 541 qgvgakraap rrapdsdsgd rghgplapas agaappsasp ssqaavaaas sssassssas 601 sssasssssas sssassssas sssasssagg aggsvasasg agerretslg praaaprgpr 661 kcarktrhae ggpepgardp apgltrylpi agvssvvala pyvnktvtgd clpvldmetg 721 higayvvlvd qtgnvadllr aaapawsrrt llpeharncv rppdyptppa sewnslwmtp 781 vgnmlfdqgt lvgaldfhgl rsrhpwsreq gapapagdap aghge
UL29 (SEQ ID NO: 10):
        MDTKPKTTTTVKVPPGPMGYVYGRACPAEGLELLSLLSARSGDA

DVAVAPLIVGLTVESGFEANVAAVVGSRTTGLGGTAVSLKLMPSHYSPSVYVFHGGRH

LAPSTQAPNLTRLCERARPHFGFADYAPRPCDLKHETTGDALCERLGLDPDRALLYLV

ITEGFREAVCISNTFLHLGGMDKVTIGDAEVHRIPVYPLQMFMPDFSRVIADPFNCNH

RSIGENFNYPLPFFNRPLARLLFEAVVGPAAVALRARNVDAVARAAAHLAFDENHEGA

ALPADITFTAFEASQGKPQRGARDAGNKGPAGGFEQRLASVMAGDAALALESIVSMAV

FDEPPPDITTWPLLEGQETPAARAGAVGAYLARAAGLVGAMVFSTNSALHLTEVDDAG

RADPKDHSKPSFYRFFLVPGTHVAANPQLDREGHVVPGYEGRPTAPLVGGTQEFAGEH

LAMLCGFSPALLAKMLFYLERCDGGVIVGRQEMDVERYVADSGQTDVPCNLCTFETRH

ACAHTTLMRLRARHPKFASAARGAIGVFGTMNSAYSDCDVLGNYAAFSALKRADGSEN

TRTIMQETYRAATERVMAELEALQYVDQAVPTALGRLETIIGNREALHTVVNNIKQLV
```

-continued

DREVEQLMRNLIEGRNFKFRDGLAEANHAMSLSLDPYTCGPCPLLQLLARRSNLAVYQ

DLALSQCHGVFAGQSVEGRNFRNQFQPVLRRRVMDLFNNGELSAKTLTVALSEGAAIC

APSLTAGQTAPAESSFEGDVARVTLGFPKELRVKSRVLFAGASANASEAAKARVASLQ

SAYQKPDKRVDILLGPLGFLLKQFHAVIFPNGKPPGSNQPNPQWFWTALQRNQLPARL

LSREDIETIAFIKRFSLDYGAINFINLAPNNVSELAMYYMANQILRYCDHSTYFINTL

TAVIAGSRRPPSVQAAAAWAPQGGAGLEAGARALMDSLDAHPGAWTSMFASCNLLRPV

MAARPMVVIGLSISKYYGMAGNDRVFQAGNWASLLGGKNACPLLIFDRTRKFVLACPR

AGFVCAASSLGGGAHEHSLCEQLRGIIAEGGAAVASSVFVATVKSLGPRTQQLQIEDW

LALLEDEYLSEEMMEFTTRALERGHGEWSTDAALEVAHEAEALVSQLGAAGEVFNFGD

FGDEDDHAASFGGLAAAAGAAGVARKRAFHGDDPFGEGPPEKKDLTLDML

UL39 (SEQ ID NO: 11):
MANRPAASALAGARSPSERQEPREPEVAPPGGDHVFCRKVSGVM

VLSSDPPGPAAYRISDSSFVQCGSNCSMIIDGDVARGHLRDLEGATSTGAFVAISNVA

AGGDGRTAVVALGGTSGPSATTSVGTQTSGEFLHGNPRTPEPQGPQAVPPPPPPPFPW

GHECCARRDARGGAEKDVGAAESWSDGPSSDSETEDSDSSDEDTGSETLSRSSSIWAA

GATDDDDSDSDSRSDDSVQPDVVVRRRWSDGPAPVAFPKPRRPGDSPGNPGLGAGTGP

GSATDPRASADSDSAAHAAAPQADVAPVLDSQPTVGTDPGYPVPLELTPENAEAVARF

LGDAVDREPALMLEYFCRCAREESKRVPPRTFGSAPRLTEDDFGLLNYALAEMRRLCL

DLPPVPPNAYTPYHLREYATRLVNGFKPLVRRSARLYRILGVLVHLRIRTREASFEEW

MRSKEVDLDFGLTERLREHEAQLMILAQALNPYDCLIHSTPNTLVERGLQSALKYEEF

YLKRFGGHYMESVFQMYTRIAGFLACRATRGMRHIALGRQGSWWEMFKFFFHRLYDHQ

IVPSTPAMLNLGTRNYYTSSCYLVNPQATTNQATLRAITGNVSAILARNGGIGLCMQA

FNDASPGTASIMPALKVLDSLVAAHNKQSTRPTGACVYLEPWHSDVRAVLRMKGVLAG

EEAQRCDNIFSALWMPDLFFKRLIRHLDGEKNVTWSLFDRDTSMSLADFHGEEFEKLY

EHLEAMGFGETIPIQDLAYAIVRSAATTGSPFIMFKDAVNRHYIYDTQGAAIAGSNLC

TEIVHPASKRSSGVCNLGSVNLARCVSRQTFDFGRLRDAVQACVLMVNIMIDSTLQPT

PQCTRGNDNLRSMGIGMQGLHTACLKMGLDLESAEFRDLNTHIAEVMLLAAMKTSNAL

CVRGARPFSHFKRSMYRAGRFHWERFSNASPRYEGEWEMLRQSMMKHGLRNSQFIALM

PTAASAQISDVSEGFAPLFTNLFSKVTRDGETLRPNTLLLKELERTFGGKRLLDAMDG

LEAKQWSVAQALPCLDPAHPLRRFKTAFDYDQELLIDLCADRAPYVDHSQSMTLYVTE

KADGTLPASTLVRLLVHAYKRGLKTGMYYCKVRKATNSGVFAGDDNIVCTSCAL

A fragment of the invention consists of less than the complete amino acid sequence of the corresponding protein, but includes the recited epitope or antigenic region. As is understood in the art and confirmed by assays conducted using fragments of widely varying lengths, additional sequence beyond the recited epitope can be included without hindering the immunological response. A fragment of the invention can be as few as 8 amino acids in length, or can encompass 10%, 20%, 30%, 40%, 50%, 60%, 70%, 80%, 90% or 95% of the full length of the protein.

The optimal length for the polypeptide of the invention will vary with the context and objective of the particular use, as is understood by those in the art. In some vaccine contexts, a full-length protein or large portion of the protein (e.g., up to 100 amino acids, 150 amino acids, 200 amino acids, 250 amino acids or more) provides optimal immunological stimulation, while in others, a short polypeptide (e.g., less than 50 amino acids, 40 amino acids, 30 amino acids, 20 amino acids, 15 amino acids or fewer) comprising the minimal epitope and/or a small region of adjacent sequence facilitates delivery and/or eases formation of a fusion protein or other means of combining the polypeptide with another molecule or adjuvant.

A polypeptide for use in a composition of the invention comprises an HSV polypeptide that contains an epitope or minimal stretch of amino acids sufficient to elicit an immune response. These polypeptides typically consist of such an epitope and, optionally, adjacent sequence. Those skilled in the art are aware that the HSV epitope can still be immunologically effective with a small portion of adjacent HSV or other amino acid sequence present. Accordingly, a typical polypeptide of the invention will consist essentially of the recited epitope and have a total length of up to 15, 20, 25 or 30 amino acids.

A typical embodiment of the invention is directed to a polypeptide consisting essentially of amino acids as listed in Table 1 below. More specifically, a polypeptide consisting of one of the 15 mers listed in Table 1 and, optionally, up to 15 amino acids of adjacent native sequence. A typical embodiment of the invention is directed to a polypeptide consisting essentially of amino acids 369 to 383 of UL25 (HNLFLWEDQTLLRAT; SEQ ID NO: 5). More specifically, a polypeptide consisting of 372 to 380 (FLWEDQTLL; SEQ ID NO: 1) of UL25 and, optionally, up to 15 amino acids of adjacent native sequence. In another embodiment, the invention is directed to a fragment of UL25 consisting of amino acids 405-419 (DRLDNRLQLGMLIPG; SEQ ID NO: 4). In some embodiments, the polypeptide is fused with or co-administered with a heterologous peptide. The heterologous peptide can be another epitope or unrelated sequence. The unrelated sequence may be inert or it may facilitate the immune response. In some embodiments, the epitope is part of a multi-epitopic vaccine, in which numerous epitopes are combined in one polypeptide.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. An isolated HSV polypeptide of the invention is one that has been isolated, produced or synthesized such that it is separate from a complete, native herpes simplex virus, although the isolated polypeptide may subsequently be introduced into a recombinant virus. A recombinant virus that comprises an isolated polypeptide or polynucleotide of the invention is an example of subject matter provided by the invention. Preferably, such isolated polypeptides are at least about 90% pure, more preferably at least about 95% pure and most preferably at least about 99% pure. A polynucleotide is considered to be isolated if, for example, it is cloned into a vector that is not part of the natural environment.

The polypeptide can be isolated from its naturally occurring form, produced by recombinant means or synthesized chemically. Recombinant polypeptides encoded by DNA sequences described herein can be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably the host cells employed are E. coli, yeast or a mammalian cell line such as Cos or CHO. Supernatants from the soluble host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Fragments and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain (Merrifield, 1963, J. Am. Chem. Soc. 85:2146-2149). Equipment for automated synthesis of polypeptides is commercially available from suppliers such as Perkin Elmer/Applied BioSystems Division (Foster City, Calif.), and may be operated according to the manufacturer's instructions.

Variants of the polypeptide for use in accordance with the invention can have one or more amino acid substitutions, deletions, additions and/or insertions in the amino acid sequence indicated that result in a polypeptide that retains the ability to elicit an immune response to HSV or HSV-infected cells. Such variants may generally be identified by modifying one of the polypeptide sequences described herein and evaluating the reactivity of the modified polypeptide using a known assay such as a T cell assay described herein. Polypeptide variants preferably exhibit at least about 70%, more preferably at least about 90%, and most preferably at least about 95% identity to the identified polypeptides. These amino acid substitutions include, but are not necessarily limited to, amino acid substitutions known in the art as "conservative". Those skilled in the art recognize that any substitutions are preferably made in amino acids outside of the minimal epitope identified herein.

A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

One can readily confirm the suitability of a particular variant by assaying the ability of the variant polypeptide to elicit an immune response. The ability of the variant to elicit an immune response can be compared to the response elicited by the parent polypeptide assayed under identical circumstances. One example of an immune response is a cellular immune response. The assaying can comprise performing an assay that measures T cell stimulation or activation. Examples of T cells include CD4 and CD8 T cells.

One example of a T cell stimulation assay is a cytotoxicity assay, such as that described in Koelle, D M et al., Human Immunol. 1997, 53; 195-205. In one example, the cytotoxicity assay comprises contacting a cell that presents the antigenic viral peptide in the context of the appropriate HLA molecule with a T cell, and detecting the ability of the T cell to kill the antigen presenting cell. Cell killing can be detected by measuring the release of radioactive $^{51}$Cr from the antigen presenting cell. Release of $^{51}$Cr into the medium from the antigen presenting cell is indicative of cell killing. An exemplary criterion for increased killing is a statistically significant increase in counts per minute (cpm) based on counting of $^{51}$Cr radiation in media collected from antigen presenting cells admixed with T cells as compared to control media collected from antigen presenting cells admixed with media.

Fusion Proteins

The polypeptide can be a fusion protein. In one embodiment, the fusion protein is soluble. A soluble fusion protein of the invention can be suitable for injection into a subject and for eliciting an immune response. Within certain embodiments, a polypeptide can be a fusion protein that comprises multiple polypeptides as described herein, or that comprises at least one polypeptide as described herein and an unrelated sequence. In one example, the fusion protein comprises a HSV epitope described herein (with or without flanking adjacent native sequence) fused with non-native sequence. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., 1985, Gene 40:39-46; Murphy et al., 1986, Proc. Natl. Acad. Sci. USA 83:8258-8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al., 1997, New Engl. J. Med., 336:86-9).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenza virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In some embodiments, it may be desirable to couple a therapeutic agent and a polypeptide of the invention, or to couple more than one polypeptide of the invention. For example, more than one agent or polypeptide may be coupled directly to a first polypeptide of the invention, or linkers that provide multiple sites for attachment can be used. Alternatively, a carrier can be used. Some molecules are particularly suitable for intercellular trafficking and protein delivery, including, but not limited to, VP22 (Elliott and O'Hare, 1997, Cell 88:223-233; see also Kim et al., 1997, J. Immunol. 159:1666-1668; Rojas et al., 1998, Nature Biotechnology 16:370; Kato et al., 1998, FEBS Lett. 427(2):203-208; Vives et al., 1997, J. Biol. Chem. 272(25):16010-7; Nagahara et al., 1998, Nature Med. 4(12):1449-1452).

A carrier may bear the agents or polypeptides in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088).

Polynucleotides, Vectors, Host Cells and Recombinant Viruses

The invention provides polynucleotides that encode one or more polypeptides of the invention. The complete genome sequence of HSV-2, strain HG52 (Accession No. Z86099). The polynucleotide can be included in a vector. The vector can further comprise an expression control sequence operably linked to the polynucleotide of the invention. In some embodiments, the vector includes one or more polynucleotides encoding other molecules of interest. In one embodiment, the polynucleotide of the invention and an additional polynucleotide can be linked so as to encode a fusion protein.

Within certain embodiments, polynucleotides may be formulated so to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, vaccinia or a pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

The invention also provides a host cell transformed with a vector of the invention. The transformed host cell can be used in a method of producing a polypeptide of the invention. The method comprises culturing the host cell and recovering the polypeptide so produced. The recovered polypeptide can be purified from culture supernatant.

Vectors of the invention can be used to genetically modify a cell, either in vivo, ex vivo or in vitro. Several ways of genetically modifying cells are known, including transduction or infection with a viral vector either directly or via a retroviral producer cell, calcium phosphate precipitation, fusion of the recipient cells with bacterial protoplasts containing the DNA, treatment of the recipient cells with liposomes or microspheres containing the DNA, DEAE dextran, receptor-mediated endocytosis, electroporation, micro-injection, and many other techniques known to those of skill. See, e.g., Sambrook et al. Molecular Cloning—A Laboratory Manual (2nd ed.) 1-3, 1989; and Current Protocols in Molecular Biology, F. M. Ausubel et al., eds., Greene Publishing Associates, Inc. and John Wiley & Sons, Inc., (1994 Supplement).

Examples of viral vectors include, but are not limited to retroviral vectors based on, e.g., HIV, SIV, and murine retroviruses, gibbon ape leukemia virus and other viruses such as adeno-associated viruses (AAVs) and adenoviruses. (Miller et al. 1990, Mol. Cell. Biol. 10:4239; J. Kolberg 1992, NIH Res. 4:43, and Cornetta et al. 1991, Hum. Gene Ther. 2:215). Widely used retroviral vectors include those based upon murine leukemia virus (MuLV), gibbon ape leukemia virus (GaLV), ecotropic retroviruses, simian immunodeficiency virus (SIV), human immunodeficiency virus (HIV), and combinations. See, e.g. Buchscher et al. 1992, J. Virol. 66(5): 2731-2739; Johann et al. 1992, J. Virol. 66(5):1635-1640; Sommerfelt et al. 1990, Virol. 176:58-59; Wilson et al. 1989, J. Virol. 63:2374-2378; Miller et al. 1991, J. Virol. 65:2220-2224, and Rosenberg and Fauci 1993 in Fundamental Immunology, Third Edition, W. E. Paul (ed.) Raven Press, Ltd., New York and the references therein; Miller et al. 1990, Mol. Cell. Biol. 10:4239; R. Kolberg 1992, J. NIH Res. 4:43; and Cornetta et al. 1991, Hum. Gene Ther. 2:215.

In vitro amplification techniques suitable for amplifying sequences to be subcloned into an expression vector are known. Examples of such in vitro amplification methods, including the polymerase chain reaction (PCR), ligase chain reaction (LCR), QR-replicase amplification and other RNA polymerase mediated techniques (e.g., NASBA), are found in Sambrook et al. 1989, Molecular Cloning—A Laboratory Manual (2nd Ed) 1-3; and U.S. Pat. No. 4,683,202; PCR Protocols A Guide to Methods and Applications (Innis et al. eds.) Academic Press Inc. San Diego, Calif. 1990. Improved methods of cloning in vitro amplified nucleic acids are described in U.S. Pat. No. 5,426,039.

The invention additionally provides a recombinant microorganism genetically modified to express a polynucleotide of the invention. The recombinant microorganism can be useful as a vaccine, and can be prepared using techniques known in the art for the preparation of live attenuated vaccines. Examples of microorganisms for use as live vaccines include, but are not limited to, viruses and bacteria. In a preferred embodiment, the recombinant microorganism is a virus. Examples of suitable viruses include, but are not limited to, vaccinia virus and other poxviruses.

Compositions

The invention provides compositions that are useful for treating and preventing HSV infection. The compositions can be used to inhibit viral replication and to kill virally-infected cells. In one embodiment, the composition is a pharmaceutical composition. The composition can comprise a therapeutically or prophylactically effective amount of a polypeptide, polynucleotide, recombinant virus, APC or immune cell of the invention. An effective amount is an amount sufficient to elicit or augment an immune response, e.g., by activating T cells. One measure of the activation of T cells is a cytotoxicity assay, as described in D. M. Koelle et al., 1997, Human Immunol. 53:195-205. In some embodiments, the composition is a vaccine.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

The composition of the invention can further comprise one or more adjuvants. Examples of adjuvants include, but are not limited to, helper peptide, alum, Freund's, muramyl tripeptide phosphatidyl ethanolamine or an immunostimulating complex, including cytokines. In some embodiments, such as with the use of a polynucleotide vaccine, an adjuvant such as a helper peptide or cytokine can be provided via a polynucleotide encoding the adjuvant. Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other viral antigens may be present, either incorporated into a fusion polypeptide or as a separate compound, within the composition or vaccine.

A pharmaceutical composition or vaccine may contain DNA encoding one or more of the polypeptides of the invention, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143-198, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317-321; Flexner et al., 1989, Ann. My Acad. Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242; WO 91102805; Berkner, 1988, Biotechniques 6:616-627; Rosenfeld et al., 1991, Science 252:431-434; Kolls et al., 1994, Proc. Natl. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749 and reviewed by Cohen, 1993, Science 259:1691-1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quit A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145-173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL™ adjuvants are available from Corixa Corporation (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham).

Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets HSV-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have antiviral effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998, Nature Med. 4:594-600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well-characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a polypeptide (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, Immunology and Cell Biology 75:456-460. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Administration of the Compositions

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals as well as other veterinary subjects. Preferably, the patients or subjects are human.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as HSV infection, the physician needs to evaluate the production of an immune response against the virus, progression of the disease, and any treatment-related toxicity.

For example, a vaccine or other composition containing a subunit HSV protein can include 1-10,000 micrograms of HSV protein per dose. In a preferred embodiment, 10-1000 micrograms of HSV protein is included in each dose in a more preferred embodiment 10-100 micrograms of HSV protein dose. Preferably, a dosage is selected such that a single dose will suffice or, alternatively, several doses are administered over the course of several months. For compositions containing HSV polynucleotides or peptides, similar quantities are administered per dose.

In one embodiment, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an antiviral immune response, and is at least 10-50% above the basal (i.e., untreated) level. Such vaccines should also be capable of causing an immune response that leads to an improved clinical outcome in vaccinated patients as compared to non-vaccinated patients. In general, for pharmaceutical compositions and vaccines comprising one or more polypeptides, the amount of each polypeptide present in a dose ranges from about 0.1 µg to about 5 mg per kg of host. Preferably, the amount ranges from about 10 to about 1000 µg per dose. Suitable volumes for administration will vary with the size, age and immune status of the patient, but will typically range from about 0.1 mL to about 5 mL, with volumes less than about 1 mL being most common.

Compositions comprising immune cells are preferably prepared from immune cells obtained from the subject to whom the composition will be administered. Alternatively, the immune cells can be prepared from an HLA-compatible donor. The immune cells are obtained from the subject or donor using conventional techniques known in the art, exposed to APCs modified to present an epitope of the invention, expanded ex vivo, and administered to the subject. Protocols for ex vivo therapy are described in Rosenberg et al., 1990, New England J. Med. 9:570-578. In addition, compositions can comprise APCs modified to present an epitope of the invention.

Immune cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to enrich and rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Administration by many of the routes of administration described herein or otherwise known in the art may be accomplished simply by direct administration using a needle, catheter or related device, at a single time point or at multiple time points.

In Vivo Testing of Identified Antigens

Conventional techniques can be used to confirm the in vivo efficacy of the identified HSV antigens. For example, one technique makes use of a mouse challenge model. Those skilled in the art, however, will appreciate that these methods are routine, and that other models can be used.

Once a compound or composition to be tested has been prepared, the mouse or other subject is immunized with a series of injections. For example up to 10 injections can be administered over the course of several months, typically with one to 4 weeks elapsing between doses. Following the last injection of the series, the subject is challenged with a dose of virus established to be a uniformly lethal dose. A control group receives placebo, while the experimental group is actively vaccinated. Alternatively, a study can be designed using sublethal doses. Optionally, a dose-response study can be included. The end points to be measured in this study include death and severe neurological impairment, as evidenced, for example, by spinal cord gait. Survivors can also be sacrificed for quantitative viral cultures of key organs including spinal cord, brain, and the site of injection. The quantity of virus present in ground up tissue samples can be measured. Compositions can also be tested in previously infected animals for reduction in recurrence to confirm efficacy as a therapeutic vaccine.

Efficacy can be determined by calculating the IC50, which indicates the micrograms of vaccine per kilogram body weight required for protection of 50% of subjects from death. The IC50 will depend on the challenge dose employed. In addition, one can calculate the LD50, indicating how many infectious units are required to kill one half of the subjects receiving a particular dose of vaccine. Determination of the post mortem viral titer provides confirmation that viral replication was limited by the immune system.

A subsequent stage of testing would be a vaginal inoculation challenge. For acute protection studies, mice can be used. Because they can be studied for both acute protection and prevention of recurrence, guinea pigs provide a more physiologically relevant subject for extrapolation to humans. In this type of challenge, a non-lethal dose is administered, the guinea pig subjects develop lesions that heal and recur. Measures can include both acute disease amelioration and recurrence of lesions. The intervention with vaccine or other composition can be provided before or after the inoculation, depending on whether one wishes to study prevention versus therapy.

Methods of Treatment and Prevention

The invention provides a method for treatment and/or prevention of HSV infection in a subject. The method comprises administering to the subject a composition of the invention. The composition can be used as a therapeutic or prophylactic vaccine. In one embodiment, the HSV is HSV-2. Alternatively, the HSV is HSV-1. The invention additionally provides a method for inhibiting HSV replication, for killing HSV-infected cells, for increasing secretion of lymphokines having antiviral and/or immunomodulatory activity, and for enhancing production of herpes-specific antibodies. The method comprises contacting an HSV-infected cell with an immune cell directed against an antigen of the invention, for example, as described in the Examples presented herein. The contacting can be performed in vitro or in vivo. In a preferred embodiment, the immune cell is a T cell. T cells include CD4 and CD8 T cells. Compositions of the invention can also be used as a tolerizing agent against immunopathologic disease.

In addition, the invention provides a method of producing immune cells directed against HSV. The method comprises contacting an immune cell with an HSV polypeptide of the invention. The immune cell can be contacted with the polypeptide via an antigen-presenting cell, wherein the antigen-presenting cell is modified to present an antigen included in a polypeptide of the invention. Preferably, the antigen-presenting cell is a dendritic cell. The cell can be modified by, for example, peptide loading or genetic modification with a nucleic acid sequence encoding the polypeptide. In one embodiment, the immune cell is a T cell. T cells include CD4 and CD8 T cells. Also provided are immune cells produced by the method. The immune cells can be used to inhibit HSV replication, to kill HSV-infected cells, in vitro or in vivo, to increase secretion of lymphokines having antiviral and/or immunomodulatory activity, to enhance production of herpes-specific antibodies, or in the treatment or prevention of HSV infection in a subject.

The invention also provides a diagnostic assay. The diagnostic assay can be used to identify the immunological responsiveness of a patient suspected of having a herpetic infection and to predict responsiveness of a subject to a particular course of therapy. The assay comprises exposing T cells of a subject to an antigen of the invention, in the context of an appropriate APC, and testing for immunoreactivity by, for example, measuring IFNγ, proliferation or cytotoxicity. Suitable assays are known in the art.

EXAMPLES

The following examples are presented to illustrate the present invention and to assist one of ordinary skill in making and using the same. The examples are not intended in any way to otherwise limit the scope of the invention.

Example 1

Identification of a Specific Epitope of $U_L25$ that is Highly Effective

A large quantity of 15 mers from select proteins of HSV-2 was obtained and screened using flow cytometry to identify which peptides could elicit responses from CD4+ or CD8+ T-cells obtained from infected patients meeting particular criteria relating to their history and shedding levels. The 15 mers were screened in 29 pools of up to 100 peptides each. ELISPOT technology was used to further identify individual peptides. Of the 15 mers testing positive, further analysis was used to guide identification of the minimal epitope given the patient HLA types. This was followed by confirmatory testing, which led to identification of the 9 amino acid peptide FLWEDQTLL (SEQ ID NO: 1) as the epitope within the 15 mer at amino acids 369 to 383 of $U_L25$ (SEQ ID NO: 5) identified through screening.

This 9 mer and its corresponding 15 mer were repeatedly and strongly positive and antigenic for persons with the common HLA allele A*0201, A*0202 or other HLA-A2 subtypes. About 40% of persons in several ethnic groups have the HLA A*0201 allele in their genetic background, and a very large portion of the global population exhibits one of the HLA-A2 subtypes. Accordingly, a vaccine containing this 9 amino acid epitope, or a longer variant including up to the full-length $U_L25$, would be expected to provoke or amplify CD8 T-cell responses in a relatively large proportion of the human population.

Example 2

Discovery of Specific Epitopes from HSV-2 that Activate Polyfunctional Cytotoxic T Lymphocytes Increasing evidence shows cytotoxic T cell responses are critical to the containment of HSV infections in the ganglion and in the periphery. Yet little is known about the breadth and functional diversity of HSV-specific CD8+ T cell responses in humans. We conducted an investigation to evaluate whether the ability of CD8+ T cells, specific for distinct epitopes in an individual, varied in their function. We sampled, in 55 HSV-2 seropositive persons, CD8+ T cell responses to 14 HSV-2 ORFs previously identified as immunoprevalent targets and identified >20 previously unidentified epitopes. Persons with multiple CD8+ T cell epitopes were studied further. Regardless of stimulatory epitope, peripheral HSV-2 specific CD8+ T-cells produced cytokines, such as IFN-γ, IL-2 and TNF-α, and expressed CD107a, a marker for degranulation. Decreased granzyme levels occurred in these T-cells following activation by HSV-2 specific peptides consistent with the ability of these lymphocytes to degranulate, and CFSE stained T-cells markedly reduce CFSE brightness following exposure to HSV-2 peptides, indicating their potential to proliferate. We found variability in cytokine production in T cell lines between individuals and within protein and epitope specific responses within an individual. In general, those with strong responses during initial intracellular cytokine staining (ICS) screening, tended to be polyfunctional, those with low responses (<0.05% of CD8+ T cells) tended to be more monofunctional. Individual differences in T cell lines to different epitopes were demonstrated.

Methods

Antigen Selection

14 HSV-2 ORFs were selected based on frequent CD8+ T cell responses found in HSV-2 seropositive subjects [1].

Peptide Pools

Antigenic proteins were constructed as peptide pools using HG52 sequence (Z86099) with local consensus sequence modifications. 15-mers with 11 aa overlap were combined into pools of up to 100 peptides to generate 29 pools total.

Study Subjects

| HSV-2 seropositive subjects 55 (%) | HSV-2 seronegative subjects 18 (%) |
|---|---|
| Gender N (%) | Gender N (%) |
| Female 26 (47)<br>Male 29 (53) | Female 8 (44)<br>Male 10 (56) |
| Race | Race |
| Caucasian 45 (82)<br>Non-Caucasian 10 (18) | Caucasian 14 (78)<br>Non-Caucasian 4 (22) |
| Age<br>(min: 27.8; max: 69.1;<br>median: 51.9) | Age<br>(min: 23.1; max: 60.2;<br>median: 29.8) |
| <30     2 (4)<br>31-50  24 (44)<br>>50    29 (53) | <30     10 (56)<br>31-50    6 (33)<br>>50      2 (11) |
| HSV-1 status | HSV-1 status |
| Positive 21 (38)<br>Negative 34 (62) | Positive 0 (0)<br>Negative 18 (100) |

Epitope Discovery

High throughput intracellular cytokine staining-flow cytometry (ICS) was used to detect IFN-γ, IL-2, TNF-α expression in CD8+ T cells following 6 h exposure of PBMC with HSV-2 peptides (or control antigen) in the presence of co-stimulatory antibodies (α-CD28/α-CD49d) and Brefeldin A. Cytokine responses to peptide antigen were scored positive if they differed from the negative control (p<0.02; Fisher's one-sided test); this cutoff was defined during trial and error validation studies with HSV-2 seronegative subjects and allows for a 5% false positive error rate. Peptide pools giving positive responses by ICS in HSV-2 seropositive subjects were deconvoluted using IFN-γ ELISpot to identify the causative peptide. Deconvolution cutoff was determined as at least 11 spots per well and 3-fold higher spots than DMSO (negative) control.

Examination of T Cell Function to Individual Epitopes

Identified single peptides were used to individually stimulate CD8+ T cells in subjects with multiple epitopes. These responses were analyzed by ICS to determine the polyfunctional profiles of HSV-2 specific T cells, Single peptides were also used to assess degranulation; the presence of lytic proteins granzyme B and perforin, in HSV-2 specific CD8+ T cells, was determined by flow cytometry. The proliferative capacities of HSV-2 specific T cells were determined by pre-staining peptide exposed PBMC with CFSE. A cell division index (CDI) >2 was used as a cut-off for proliferation positivity.

Results

Epitope Discovery and Prevalence

Screening PBMC of HSV-2 seropositive and seronegative subjects by high throughput ICS identified ICP0, UL39 and UL49 as the most immunoprevalent ORFs recognized by CD8+ T cells; highest responses were identified for all 3 cytokines assayed. Other tegument (e.g. UL46) and capsid (e.g. UL19, UL25) HSV-2 proteins were also highly immunoprevalent in seropositive subjects. Few responses were detected for glycoproteins gD or gJ. A small number (1-2 per ORF) of responses were identified in seronegative subjects, although these responses, in all cases, were barely above baseline levels.

More than 20 peptides were confirmed as CD8+ T cell epitopes by ELISpot and follow-up ICS. A novel epitope identified in UL25 was confirmed as a common HLA-A02 restricted epitope; it was confirmed to produce responses in at least 5 subjects. A common epitope was identified from UL49 in at least 6 subjects possessing HLA-B07, consistent with previous studies [2].

TABLE 1

CD8+ T cell epitopes in HSV-2 ORFs

| ORF | PEPTIDE EPITOPE | LOCATION IN ORF | # SUB-JECTS | PRE-DICTED HLA |
|---|---|---|---|---|
| UL19 | AFEDRSYPAVFYLLQ<br>(SEQ ID NO: 12) | 617-631 | 1 | B08 |
| UL25 | HNLFLWEDQTLLRAT<br>(SEQ ID NO: 5) | 369-383 | 5 | A02 |
|  | DRLDNRLQLGMLIPG<br>(SEQ ID NO: 4) | 405-419 | 1 | A02 |
| UL46 | RLGPADRRFVALSGS<br>(SEQ ID NO: 13) | 249-263 | 3 | B07 |
|  | AQREAAGVYDAVRTW<br>(SEQ ID NO: 14) | 533-547 | 2 | A68 |
| UL49 | PMRARPRGEVRFLHY<br>(SEQ ID NO: 15) | 45-59 | 6 | B07 |
|  | ARPRRSASVAGSHGPG<br>(SEQ ID NO: 16) | 81-96 | 2 | B07 |
|  | HGPGPARAPPPPGGPV<br>(SEQ ID NO: 17) | 93-108 | 1 | B07 |
|  | PKASATPATDPARGR<br>(SEQ ID NO: 18) | 129-143 | 1 | B07 |
|  | KNLLQRANELVNPDA<br>(SEQ ID NO: 19) | 249-263 | 1 | B08 |
| ICP0 | EAGLMDAATPPARPPA<br>(SEQ ID NO: 20) | 77-92 | 1 | A30 |
|  | LHPFCIPCMKTWIPL<br>(SEQ ID NO: 21) | 145-159 | 1 | A03 |
|  | DFIWTGNPRTAPRSL<br>(SEQ ID NO: 22) | 209-223 | 2 | B07 |
|  | LPIAGVSSVVALAPY<br>(SEQ ID NO: 23) | 689-703 | 1 | B35 |
|  | DMETGHIGAYVVLVD<br>(SEQ ID NO: 24) | 717-731 | 1 | B39 |
|  | GHIGAYVVLVDQTGN<br>(SEQ ID NO: 25) | 721-735 | 1 | A68 |
|  | RAAAPAWSRRTLLPE<br>(SEQ ID NO: 26) | 741-755 | 3 | B07 |
|  | PVGNMLFDQGTLVGA<br>(SEQ ID NO: 27) | 779-793 | 1 | A02 |
| UL39 | LMLEYFCRCAREESK<br>(SEQ ID NO: 28) | 346-359 | 1 | A03 |
|  | GVLVHLRIRTREASF<br>(SEQ ID NO: 29) | 433-447 | 1 | B62 |
|  | FGGHYMESVFQMYTR<br>(SEQ ID NO: 30) | 515-529 | 1 | A01 |

TABLE 1-continued

CD8+ T cell epitopes in HSV-2 ORFs

| ORF | PEPTIDE EPITOPE | LOCATION IN ORF | # SUB-JECTS | PRE-DICTED HLA |
|---|---|---|---|---|
| | SMSLADFHGEEFEKL (SEQ ID NO: 31) | 725-739 | 1 | B07 |
| | KTSNALCVRGARPFS (SEQ ID NO: 32) | 911-925 | 1 | A31 |
| UL29 | CPLLIFDRTRKFVLA (SEQ ID NO: 33) | 1013-1027 | 1 | ? |

Summary

We detected HSV-2 specific CD8+ T cells in HSV-2 seropositive subjects, and isolated more than 20 unique CD8+ T cell epitopes, many of which have never been previously described. With the peptide epitopes, we assessed polyfunctionality, degranulation potential and proliferation capacity of HSV-2 specific T cells, and examined intra- and inter-individual differences. A mixture of mono- and polyfunctional CD8+ T cells were found for all subjects tested, although the proportions of monofunctional cells varied. Although some modest inter-individual differences were observed in the functional phenotypes, all polyfunctional HSV-2 specific cells predominantly produced IFN-γ. Granzyme B was identified in HSV-2 specific T cells, and these cells could degranulate. All individuals had CD8+ T cells that could proliferate, although some intra-individual differences were apparent for at least one subject.

Polyfunctional T Cells

Single peptides identified during this study were used to activate epitope specific CD8+ T cells. Antigen specific CD8+ T cells were identified using a gating strategy. 15 possible distinct combinations of the 4 functional markers were observed, A mixture of monofunctional and polyfunctional HSV-2-specific CD8+ T cells were identified for all subjects. The polyfunctional profiles of responding cells, with reference to the expression of IFN-γ, IL2, and TNF-α, and the mobilization of CD107a were determined.

Intra-Individual Comparison of HSV-2 Epitope Specific T Cells

One individual was identified with four HLA-B07 restricted epitopes within UL49. This individual allowed the comparison of epitope specific responses without influence from the kinetics of ORF expression, or from genetic and HLA differences. UL4945-59 was the immunodominant epitope in this individual, producing the largest detectable response in Elispot and ICS assays. The cells responding to this epitope showed some characteristic differences from other tested epitopes: they comprised less CD107a positive cells relative to IFN-γ+ cells, contained higher levels of IFN-γ, but not other cytokines, and they comprised less monofunctional cells. The unique properties of the epitope and/or the T cell receptors that recognize it, likely influence the functional characteristics of the T cells.

Inter-Individual Comparison of HSV-2 Epitope Specific T Cells

A similar observation was made for other subjects, with responses to multiple epitopes, indicating polyfunctionality was not restricted to UL49-specific or HLA-B07 restricted T cells. While differences were seen between epitopes and individuals, polyfunctional cells, in all cases, were predominantly IFN-γ+, and monofunctional cells were mostly IFN-γ+ or CD107a+, consistent with a Th1 "effector" T cell phenotype.

Degranulation

CD107a mobilization is an indicator of degranulation but does not confirm that lytic molecules are stored within cells. To assess whether HSV-2 specific T cells store lytic proteins, single peptides were used to activate and identify HSV-2 specific CD8+ T cells during flow cytometric analyses of granzyme B and perforin expression. Activated CD8+ T cells were identified by gating on IFN-γ+CD3+CD8+ T cells following the gating strategy. Regardless of epitope or individual: Few activated HSV-2 specific T cells had detectable Perf; 2.2% (median; range 0-9.1%) were GrzB-Perf+IFN-γ+ and 6.5% (median; range 1.6-13.3%) were GrzB+Perf+IFN-γ+; GrzB+ cells were more frequent, with 42.3% (median; range 34.1-50.8%) of responding T cells having a GrzB+Perf-IFN-γ+ phenotype, and similar levels of IFN-γ+ T cells with neither GrzB nor Perf (median 47.6%; range 40.0-53.2%). Confirming CD107a mobilization in epitope specific T cells, ICS was performed on PBMC exposed to the same peptides. An increase in IFN-γ+ T cells was observed in both GrzB+ and GrzB– and perforin+ populations in all tested subjects.

Proliferation

To evaluate the proliferative capacity of HSV-2 specific CD8+ T cells, we utilized CFSE to stain PBMC prior to epitope specific stimulation. Four subjects were each tested with two distinct CD8+ T cell peptides; a CDI index >2 was seen with all HSV-2 epitopes from all four subjects (range=2.1-14, median=7). Variability was seen with 4 distinct epitopes with UL49 of a single subject. CD8+ T cells that recognized UL4945-49 did proliferate (CDI=8.7), but CDI values were below threshold for peptides UL4981-96, UL4993-108 and UL49129-143 (respective CDI=1.8, 1.4 and 1.6). Since T cells specific for UL4945-49 are more abundant that those specific for the other epitopes, the ability of these cells to proliferate likely reflects the epitope dominance observed within UL49.

REFERENCES

1. Hosken et al., 2006. Diversity of the CD8+ T-cell response to herpes simplex virus type 2 proteins among persons with genital herpes. J Virol 80:5509.

2. Koelle et al., 2001. CD8 CTL from genital herpes simplex lesions: recognition of viral tegument and immediate early proteins and lysis of infected cutaneous cells. J Immunol 166:4049.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of enhancing proliferation of herpes simplex virus type 2 (HSV-2)-specific T cells from a subject expressing human leukocyte antigen (HLA) type B08 comprising contacting the HSV-specific T cells with a polypeptide consisting of AFEDRSYPAVFYLLQ (SEQ ID NO: 12) and up to 15 amino acids of adjacent native sequence of $U_L$ 19 (SEQ ID NO: 6), and wherein said T cells are contacted with said polypeptide in an amount sufficient to enhance proliferation of said HSV-2-specific T cells.

2. A method of inducing an immune response to herpes simplex virus type 2 (HSV-2) in a subject comprising administering a polypeptide consisting of AFEDRSYPAVFYLLQ (SEQ ID NO: 12) and up to 15 amino acids of adjacent native sequence of $U_L$ 19 (SEQ ID NO: 6) to the subject, wherein the subject is a human expressing human leukocyte antigen (HLA) type B08, and wherein the polypeptide is administered in an amount sufficient to induce an immune response in said subject.

3. A method of treating an HSV-2 infection in a subject comprising administering a therapeutically effective amount of a polypeptide consisting of AFEDRSYPAVFYLLQ (SEQ ID NO: 12) and up to 15 amino acids of adjacent native sequence of $U_L$ 19 (SEQ ID NO: 6) to the subject, wherein the subject is a human expressing human leukocyte antigen (HLA) type B08, and wherein the therapeutically effective dose of said polypeptide is administered in amount sufficient to treat an HSV-2 infection in said subject.

4. The method of claim 2, further comprising administering an adjuvant to the subject.

5. The method of claim 1, further comprising administering an adjuvant to the subject.

6. The method of claim 3, further comprising administering an adjuvant to the subject.

7. The method of claim 1, wherein the polypeptide consists of SEQ ID NO: 12 and up to 10 amino acids of adjacent native sequence of SEQ ID NO: 6.

8. The method of claim 2, wherein the polypeptide consists of SEQ ID NO: 12 and up to 10 amino acids of adjacent native sequence of SEQ ID NO: 6.

9. The method of claim 3, wherein the polypeptide consists of SEQ ID NO: 12 and up to 10 amino acids of adjacent native sequence of SEQ ID NO: 6.

10. The method of claim 1, wherein the polypeptide is administered in the form of a pharmaceutically acceptable salt.

11. The method of claim 2, wherein the polypeptide is administered in the form of a pharmaceutically acceptable salt.

12. The method of claim 3, wherein the polypeptide is administered in the form of a pharmaceutically acceptable salt.

13. The method of claim 1, wherein the polypeptide is co-administered with a heterologous peptide.

14. The method of claim 2, wherein the polypeptide is co-administered with a heterologous peptide.

15. The method of claim 3, wherein the polypeptide is co-administered with a heterologous peptide.

16. The method of claim 13, wherein the heterologous peptide is another HSV epitope.

17. The method of claim 13, wherein the heterologous peptide is an unrelated sequence that facilitates an immune response.

18. The method of claim 14, wherein the heterologous peptide is another HSV epitope.

19. The method of claim 14, wherein the heterologous peptide is an unrelated sequence that facilitates an immune response.

20. The method of claim 15, wherein the heterologous peptide is another HSV epitope.

21. The method of claim 15, wherein the heterologous peptide is an unrelated sequence that facilitates an immune response.

* * * * *

SEQUENCE LISTING

<160> NUMBER OF SEQ ID NOS: 33

<210> SEQ ID NO 1
<211> LENGTH: 9
<212> TYPE: PRT
<213> ORGANISM: herpes simplex virus 2

<400> SEQUENCE: 1

Phe Leu Trp Glu Asp Gln Thr Leu Leu
1               5

<210> SEQ ID NO 2
<211> LENGTH: 585
<212> TYPE: PRT
<213> ORGANISM: herpes simplex virus 2

<400> SEQUENCE: 2

Met Asp Pro Tyr Tyr Pro Phe Asp Ala Leu Asp Val Trp Glu His Arg
1               5                   10                  15

Arg Phe Ile Val Ala Asp Ser Arg Ser Phe Ile Thr Pro Glu Phe Pro
                20                  25                  30

Arg Asp Phe Trp Met Leu Pro Val Phe Asn Ile Pro Arg Glu Thr Ala
            35                  40                  45

Ala Glu Arg Ala Ala Val Leu Gln Ala Gln Arg Thr Ala Ala Ala Ala
        50                  55                  60

Ala Leu Glu Asn Ala Ala Leu Gln Ala Ala Glu Leu Pro Val Asp Ile
65                  70                  75                  80

Glu Arg Arg Ile Arg Pro Ile Glu Gln Gln Val His His Ile Ala Asp
                85                  90                  95

Ala Leu Glu Ala Leu Glu Thr Ala Ala Ala Ala Glu Glu Ala Asp
                100                 105                 110

Ala Ala Arg Asp Ala Glu Ala Arg Gly Glu Gly Ala Ala Asp Gly Ala
            115                 120                 125

Ala Pro Ser Pro Thr Ala Gly Pro Ala Ala Glu Met Glu Val Gln
        130                 135                 140

Ile Val Arg Asn Asp Pro Pro Leu Arg Tyr Asp Thr Asn Leu Pro Val
145                 150                 155                 160

Asp Leu Leu His Met Val Tyr Ala Gly Arg Gly Ala Ala Gly Ser Ser
                165                 170                 175

Gly Val Val Phe Gly Thr Trp Tyr Arg Thr Ile Gln Glu Arg Thr Ile
            180                 185                 190

Ala Asp Phe Pro Leu Thr Thr Arg Ser Ala Asp Phe Arg Asp Gly Arg
        195                 200                 205

Met Ser Lys Thr Phe Met Thr Ala Leu Val Leu Ser Leu Gln Ser Cys
    210                 215                 220

Gly Arg Leu Tyr Val Gly Gln Arg His Tyr Ser Ala Phe Glu Cys Ala
225                 230                 235                 240

Val Leu Cys Leu Tyr Leu Leu Tyr Arg Thr Thr His Glu Ser Ser Pro
                245                 250                 255

Asp Arg Asp Arg Ala Pro Val Ala Phe Gly Asp Leu Leu Ala Arg Leu
            260                 265                 270

Pro Arg Tyr Leu Ala Arg Leu Ala Ala Val Ile Gly Asp Glu Ser Gly
        275                 280                 285

Arg Pro Gln Tyr Arg Tyr Arg Asp Asp Lys Leu Pro Lys Ala Gln Phe
    290                 295                 300

Ala Ala Ala Gly Gly Arg Tyr Glu His Gly Ala Leu Ala Thr His Val

```
            305                 310                 315                 320
Val Ile Ala Thr Leu Val Arg His Gly Val Leu Pro Ala Ala Pro Gly
                325                 330                 335

Asp Val Pro Arg Asp Thr Ser Thr Arg Val Asn Pro Asp Asp Val Ala
                340                 345                 350

His Arg Asp Asp Val Asn Arg Ala Ala Ala Phe Leu Ala Arg Gly
                355                 360                 365

His Asn Leu Phe Leu Trp Glu Asp Gln Thr Leu Leu Arg Ala Thr Ala
            370                 375                 380

Asn Thr Ile Thr Ala Leu Ala Val Leu Arg Arg Leu Leu Ala Asn Gly
385                 390                 395                 400

Asn Val Tyr Ala Asp Arg Leu Asp Asn Arg Leu Gln Leu Gly Met Leu
                405                 410                 415

Ile Pro Gly Ala Val Pro Ala Glu Ala Ile Ala Arg Gly Ala Ser Gly
                420                 425                 430

Leu Asp Ser Gly Ala Ile Lys Ser Gly Asp Asn Asn Leu Glu Ala Leu
                435                 440                 445

Cys Val Asn Tyr Val Leu Pro Leu Tyr Gln Ala Asp Pro Thr Val Glu
                450                 455                 460

Leu Thr Gln Leu Phe Pro Gly Leu Ala Ala Leu Cys Leu Asp Ala Gln
465                 470                 475                 480

Ala Gly Arg Pro Leu Ala Ser Thr Arg Val Val Asp Met Ser Ser
                485                 490                 495

Gly Ala Arg Gln Ala Ala Leu Val Arg Leu Thr Ala Leu Glu Leu Ile
                500                 505                 510

Asn Arg Thr Arg Thr Asn Thr Thr Pro Val Gly Glu Ile Ile Asn Ala
            515                 520                 525

His Asp Ala Leu Gly Ile Gln Tyr Glu Gln Gly Pro Gly Leu Leu Ala
            530                 535                 540

Gln Gln Ala Arg Ile Gly Leu Ala Ser Asn Thr Lys Arg Phe Ala Thr
545                 550                 555                 560

Phe Asn Val Gly Ser Asp Tyr Asp Leu Leu Tyr Phe Leu Cys Leu Gly
                565                 570                 575

Phe Ile Pro Gln Tyr Leu Ser Val Ala
                580                 585

<210> SEQ ID NO 3
<211> LENGTH: 580
<212> TYPE: PRT
<213> ORGANISM: herpes simplex virus 1

<400> SEQUENCE: 3

Met Asp Pro Tyr Cys Pro Phe Asp Ala Leu Asp Val Trp Glu His Arg
1               5                   10                  15

Arg Phe Ile Val Ala Asp Ser Arg Asn Phe Ile Thr Pro Glu Phe Pro
                20                  25                  30

Arg Asp Phe Trp Met Ser Pro Val Phe Asn Leu Pro Arg Glu Thr Ala
            35                  40                  45

Ala Glu Gln Val Val Leu Gln Ala Gln Arg Thr Ala Ala Ala
        50                  55                  60

Ala Leu Glu Asn Ala Ala Met Gln Ala Ala Glu Leu Pro Val Asp Ile
65              70                  75                  80

Glu Arg Arg Leu Arg Pro Ile Glu Arg Asn Val His Glu Ile Ala Gly
                85                  90                  95
```

```
Ala Leu Glu Ala Leu Glu Thr Ala Ala Ala Ala Glu Glu Ala Asp
                100                 105                 110

Ala Ala Arg Gly Asp Glu Pro Ala Gly Gly Asp Gly Gly Ala Pro
            115                 120                 125

Pro Gly Leu Ala Val Ala Glu Met Glu Val Gln Ile Val Arg Asn Asp
130                 135                 140

Pro Pro Leu Arg Tyr Asp Thr Asn Leu Pro Val Asp Leu Leu His Met
145                 150                 155                 160

Val Tyr Ala Gly Arg Gly Ala Thr Gly Ser Ser Gly Val Val Phe Gly
                165                 170                 175

Thr Trp Tyr Arg Thr Ile Gln Asp Arg Thr Ile Thr Asp Phe Pro Leu
            180                 185                 190

Thr Thr Arg Ser Ala Asp Phe Arg Asp Gly Arg Met Ser Lys Thr Phe
        195                 200                 205

Met Thr Ala Leu Val Leu Ser Leu Gln Ala Cys Gly Arg Leu Tyr Val
    210                 215                 220

Gly Gln Arg Arg Tyr Ser Ala Phe Glu Cys Ala Val Leu Cys Leu Tyr
225                 230                 235                 240

Leu Leu Tyr Arg Asn Thr His Gly Ala Ala Asp Asp Ser Asp Arg Ala
                245                 250                 255

Pro Val Thr Phe Gly Asp Leu Leu Gly Arg Leu Pro Arg Tyr Leu Ala
            260                 265                 270

Cys Leu Ala Ala Val Ile Gly Thr Glu Gly Gly Arg Pro Gln Tyr Arg
        275                 280                 285

Tyr Arg Asp Asp Lys Leu Pro Lys Thr Gln Phe Ala Ala Gly Gly Gly
    290                 295                 300

Arg Tyr Glu His Gly Ala Leu Ala Ser His Ile Val Ile Ala Thr Leu
305                 310                 315                 320

Met His His Gly Val Leu Pro Ala Ala Pro Gly Asp Val Pro Arg Asp
                325                 330                 335

Ala Ser Thr His Val Asn Pro Asp Gly Val Ala His His Asp Asp Ile
            340                 345                 350

Asn Arg Ala Ala Ala Phe Leu Ser Arg Gly His Asn Leu Phe Leu
        355                 360                 365

Trp Glu Asp Gln Thr Leu Leu Arg Ala Thr Ala Asn Thr Ile Thr Ala
370                 375                 380

Leu Gly Val Ile Gln Arg Leu Leu Ala Asn Gly Asn Val Tyr Ala Asp
385                 390                 395                 400

Arg Leu Asn Asn Arg Leu Gln Leu Gly Met Leu Ile Pro Gly Ala Val
                405                 410                 415

Pro Ser Glu Ala Ile Ala Arg Gly Ala Ser Gly Ser Asp Ser Gly Ala
            420                 425                 430

Ile Lys Ser Gly Asp Asn Asn Leu Glu Ala Leu Cys Ala Asn Tyr Val
        435                 440                 445

Leu Pro Leu Tyr Arg Ala Asp Pro Ala Val Glu Leu Thr Gln Leu Phe
    450                 455                 460

Pro Gly Leu Ala Ala Leu Cys Leu Asp Ala Gln Ala Gly Arg Pro Val
465                 470                 475                 480

Gly Ser Thr Arg Arg Val Val Asp Met Ser Ser Gly Ala Arg Gln Ala
                485                 490                 495

Ala Leu Val Arg Leu Thr Ala Leu Glu Leu Ile Asn Arg Thr Arg Thr
            500                 505                 510

Asn Pro Thr Pro Val Gly Glu Val Ile His Ala His Asp Ala Leu Ala
```

```
                515                 520                 525
Ile Gln Tyr Glu Gln Gly Leu Gly Leu Leu Ala Gln Gln Ala Arg Ile
            530                 535                 540
Gly Leu Gly Ser Asn Thr Lys Arg Phe Ser Ala Phe Asn Val Ser Ser
545                 550                 555                 560
Asp Tyr Asp Met Leu Tyr Phe Leu Cys Leu Gly Phe Ile Pro Gln Tyr
                565                 570                 575
Leu Ser Ala Val
            580

<210> SEQ ID NO 4
<211> LENGTH: 15
<212> TYPE: PRT
<213> ORGANISM: herpes simplex virus 2

<400> SEQUENCE: 4

Asp Arg Leu Asp Asn Arg Leu Gln Leu Gly Met Leu Ile Pro Gly
1               5                   10                  15

<210> SEQ ID NO 5
<211> LENGTH: 15
<212> TYPE: PRT
<213> ORGANISM: herpes simplex virus 2

<400> SEQUENCE: 5

His Asn Leu Phe Leu Trp Glu Asp Gln Thr Leu Leu Arg Ala Thr
1               5                   10                  15

<210> SEQ ID NO 6
<211> LENGTH: 1374
<212> TYPE: PRT
<213> ORGANISM: herpes simplex virus 2

<400> SEQUENCE: 6

Met Ala Ala Pro Ala Arg Asp Pro Pro Gly Tyr Arg Tyr Ala Ala Ala
1               5                   10                  15
Ile Leu Pro Thr Gly Ser Ile Leu Ser Thr Ile Glu Val Ala Ser His
                20                  25                  30
Arg Arg Leu Phe Asp Phe Phe Ala Ala Val Arg Ser Asp Glu Asn Ser
            35                  40                  45
Leu Tyr Asp Val Glu Phe Asp Ala Leu Leu Gly Ser Tyr Cys Asn Thr
        50                  55                  60
Leu Ser Leu Val Arg Phe Leu Glu Leu Gly Leu Ser Val Ala Cys Val
65                  70                  75                  80
Cys Thr Lys Phe Pro Glu Leu Ala Tyr Met Asn Glu Gly Arg Val Gln
                85                  90                  95
Phe Glu Val His Gln Pro Leu Ile Ala Arg Asp Gly Pro His Pro Val
            100                 105                 110
Glu Gln Pro Val His Asn Tyr Met Thr Lys Val Ile Asp Arg Arg Ala
        115                 120                 125
Leu Asn Ala Ala Phe Ser Leu Ala Thr Glu Ala Ile Ala Leu Leu Thr
    130                 135                 140
Gly Glu Ala Leu Asp Gly Thr Gly Ile Ser Leu His Arg Gln Leu Arg
145                 150                 155                 160
Ala Ile Gln Gln Leu Ala Arg Asn Val Gln Ala Val Leu Gly Ala Phe
                165                 170                 175
Glu Arg Gly Thr Ala Asp Gln Met Leu His Val Leu Leu Glu Lys Ala
            180                 185                 190
```

```
Pro Pro Leu Ala Leu Leu Pro Met Gln Arg Tyr Leu Asp Asn Gly
            195                 200                 205

Arg Leu Ala Thr Arg Val Ala Arg Ala Thr Leu Val Ala Glu Leu Lys
    210                 215                 220

Arg Ser Phe Cys Asp Thr Ser Phe Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
            260                 265                 270

Pro Val Asp Gly Val Leu Val Thr Thr Ala Ala Ile Lys Gln Arg Leu
            275                 280                 285

Leu Gln Ser Phe Leu Lys Val Glu Asp Thr Glu Ala Asp Val Pro Val
        290                 295                 300

Thr Tyr Gly Glu Met Val Leu Asn Gly Ala Asn Leu Val Thr Ala Leu
305                 310                 315                 320

Val Met Gly Lys Ala Val Arg Ser Leu Asp Asp Val Gly Arg His Leu
                325                 330                 335

Leu Asp Met Gln Glu Glu Gln Leu Glu Ala Asn Arg Glu Thr Leu Asp
            340                 345                 350

Glu Leu Glu Ser Ala Pro Gln Thr Thr Arg Val Arg Ala Asp Leu Val
        355                 360                 365

Ala Ile Gly Asp Arg Leu Val Phe Leu Glu Ala Leu Glu Arg Arg Ile
370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
                405                 410                 415

Ala Ala His Ala Gly Asp Leu Val Pro Ala Pro Gly His Pro Glu Pro
            420                 425                 430

Arg Ala Phe Pro Pro Arg Gln Leu Phe Phe Trp Gly Lys Asp His Gln
        435                 440                 445

Val Leu Arg Leu Ser Met Glu Asn Ala Val Gly Thr Val Cys His Pro
450                 455                 460

Ser Leu Met Asn Ile Asp Ala Ala Val Gly Gly Val Asn His Asp Pro
465                 470                 475                 480

Val Glu Ala Ala Asn Pro Tyr Gly Ala Tyr Val Ala Ala Pro Ala Gly
                485                 490                 495

Pro Gly Ala Asp Met Gln Gln Arg Phe Leu Asn Ala Trp Arg Gln Arg
            500                 505                 510

Leu Ala His Gly Arg Val Arg Trp Val Ala Glu Cys Gln Met Thr Ala
        515                 520                 525

Glu Gln Phe Met Gln Pro Asp Asn Ala Asn Leu Ala Leu Glu Leu His
530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
                565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
        595                 600                 605
```

-continued

```
Ala Thr Ile Ala Ala Val Arg Gly Ala Phe Glu Asp Arg Ser Tyr Pro
610             615                 620
Ala Val Phe Tyr Leu Leu Gln Ala Ala Ile His Gly Asn Glu His Val
625             630                 635                 640
Phe Cys Ala Leu Ala Arg Leu Val Thr Gln Cys Ile Thr Ser Tyr Trp
                645                 650                 655
Asn Asn Thr Arg Cys Ala Ala Phe Val Asn Asp Tyr Ser Leu Val Ser
                660                 665                 670
Tyr Ile Val Thr Tyr Leu Gly Gly Asp Leu Pro Glu Glu Cys Met Ala
                675                 680                 685
Val Tyr Arg Asp Leu Val Ala His Val Glu Ala Leu Ala Gln Leu Val
690                 695                 700
Asp Asp Phe Thr Leu Pro Gly Pro Glu Leu Gly Gln Ala Gln Ala
705                 710                 715                 720
Glu Leu Asn His Leu Met Arg Asp Pro Ala Leu Pro Pro Leu Val
                725                 730                 735
Trp Asp Cys Asp Gly Leu Met Arg His Ala Ala Leu Asp Arg His Arg
                740                 745                 750
Asp Cys Arg Ile Asp Ala Gly Gly His Glu Pro Val Tyr Ala Ala Ala
                755                 760                 765
Cys Asn Val Ala Thr Ala Asp Phe Asn Arg Asn Asp Gly Arg Leu Leu
770                 775                 780
His Asn Thr Gln Ala Arg Ala Ala Asp Ala Ala Asp Arg Pro His
785                 790                 795                 800
Arg Pro Ala Asp Trp Thr Val His His Lys Ile Tyr Tyr Val Leu
                805                 810                 815
Val Pro Ala Phe Ser Arg Gly Arg Cys Cys Thr Ala Gly Val Arg Phe
                820                 825                 830
Asp Arg Val Tyr Ala Thr Leu Gln Asn Met Val Val Pro Glu Ile Ala
                835                 840                 845
Pro Gly Glu Glu Cys Pro Ser Asp Pro Val Thr Asp Pro Ala His Pro
850                 855                 860
Leu His Pro Ala Asn Leu Val Ala Asn Thr Val Lys Arg Met Phe His
865                 870                 875                 880
Asn Gly Arg Val Val Val Asp Gly Pro Ala Met Leu Thr Leu Gln Val
                885                 890                 895
Leu Ala His Asn Met Ala Glu Arg Thr Thr Ala Leu Leu Cys Ser Ala
                900                 905                 910
Ala Pro Asp Ala Gly Ala Asn Thr Ala Ser Thr Ala Asn Met Arg Ile
                915                 920                 925
Phe Asp Gly Ala Leu His Ala Gly Val Leu Leu Met Ala Pro Gln His
                930                 935                 940
Leu Asp His Thr Ile Gln Asn Gly Glu Tyr Phe Tyr Val Leu Pro Val
945                 950                 955                 960
His Ala Leu Phe Ala Gly Ala Asp His Val Ala Asn Ala Pro Asn Phe
                965                 970                 975
Pro Pro Ala Leu Arg Asp Leu Ala Arg Asp Val Pro Leu Val Pro Pro
                980                 985                 990
Ala Leu Gly Ala Asn Tyr Phe Ser  Ser Ile Arg Gln Pro  Val Val Gln
                995                 1000                1005
His Ala  Arg Glu Ser Ala Ala  Gly Glu Asn Ala Leu  Thr Tyr Ala
                1010                1015                1020
Leu Met  Ala Gly Tyr Phe Lys  Met Ser Pro Val Ala  Leu Tyr His
```

|  |  |  | 1025 |  |  |  | 1030 |  |  |  | 1035 |  |  |
|---|---|---|---|---|---|---|---|---|---|---|---|---|---|

Gln Leu Lys Thr Gly Leu His Pro Gly Phe Gly Phe Thr Val Val
    1040                      1045                      1050

Arg Gln Asp Arg Phe Val Thr Glu Asn Val Leu Phe Ser Glu Arg
    1055                      1060                      1065

Ala Ser Glu Ala Tyr Phe Leu Gly Gln Leu Gln Val Ala Arg His
    1070                      1075                      1080

Glu Thr Gly Gly Gly Val Asn Phe Thr Leu Thr Gln Pro Arg Gly
    1085                      1090                      1095

Asn Val Asp Leu Gly Val Gly Tyr Thr Ala Val Ala Ala Thr Gly
    1100                      1105                      1110

Thr Val Arg Asn Pro Val Thr Asp Met Gly Asn Leu Pro Gln Asn
    1115                      1120                      1125

Phe Tyr Leu Gly Arg Gly Ala Pro Pro Leu Leu Asp Asn Ala Ala
    1130                      1135                      1140

Ala Val Tyr Leu Arg Asn Ala Val Val Ala Gly Asn Arg Leu Gly
    1145                      1150                      1155

Pro Ala Gln Pro Leu Pro Val Phe Gly Cys Ala Gln Val Pro Arg
    1160                      1165                      1170

Arg Ala Gly Met Asp His Gly Gln Asp Ala Val Cys Glu Phe Ile
    1175                      1180                      1185

Ala Thr Pro Val Ala Thr Asp Ile Asn Tyr Phe Arg Arg Pro Cys
    1190                      1195                      1200

Asn Pro Arg Gly Arg Ala Ala Gly Gly Val Tyr Ala Gly Asp Lys
    1205                      1210                      1215

Glu Gly Asp Val Ile Ala Leu Met Tyr Asp His Gly Gln Ser Asp
    1220                      1225                      1230

Pro Ala Arg Pro Phe Ala Ala Thr Ala Asn Pro Trp Ala Ser Gln
    1235                      1240                      1245

Arg Phe Ser Tyr Gly Asp Leu Leu Tyr Asn Gly Ala Tyr His Leu
    1250                      1255                      1260

Asn Gly Ala Ser Pro Val Leu Ser Pro Cys Phe Lys Phe Phe Thr
    1265                      1270                      1275

Ala Ala Asp Ile Thr Ala Lys His Arg Cys Leu Glu Arg Leu Ile
    1280                      1285                      1290

Val Glu Thr Gly Ser Ala Val Ser Thr Ala Thr Ala Ala Ser Asp
    1295                      1300                      1305

Val Gln Phe Lys Arg Pro Pro Gly Cys Arg Glu Leu Val Glu Asp
    1310                      1315                      1320

Pro Cys Gly Leu Phe Gln Glu Ala Tyr Pro Ile Thr Cys Ala Ser
    1325                      1330                      1335

Asp Pro Ala Leu Leu Arg Ser Ala Arg Asp Gly Glu Ala His Ala
    1340                      1345                      1350

Arg Glu Thr His Phe Thr Gln Tyr Leu Ile Tyr Asp Ala Ser Pro
    1355                      1360                      1365

Leu Lys Gly Leu Ser Leu
    1370

<210> SEQ ID NO 7
<211> LENGTH: 722
<212> TYPE: PRT
<213> ORGANISM: herpes simplex virus 2

<400> SEQUENCE: 7

-continued

```
Met Gln Arg Arg Ala Arg Gly Ala Ser Ser Leu Arg Leu Ala Arg Cys
1               5                   10                  15

Leu Thr Pro Ala Asn Leu Ile Arg Gly Ala Asn Ala Gly Val Pro Glu
            20                  25                  30

Arg Arg Ile Phe Ala Gly Cys Leu Leu Pro Thr Pro Glu Gly Leu Leu
            35                  40                  45

Ser Ala Ala Val Gly Val Leu Arg Gln Arg Ala Asp Asp Leu Gln Pro
50                  55                  60

Ala Phe Leu Thr Gly Ala Asp Arg Ser Val Arg Leu Ala Ala Arg His
65                  70                  75                  80

His Asn Thr Val Pro Glu Ser Leu Ile Val Asp Gly Leu Ala Ser Asp
                85                  90                  95

Pro His Tyr Asp Tyr Ile Arg His Tyr Ala Ser Ala Ala Lys Gln Ala
            100                 105                 110

Leu Gly Glu Val Glu Leu Ser Gly Gln Leu Ser Arg Ala Ile Leu
            115                 120                 125

Ala Gln Tyr Trp Lys Tyr Leu Gln Thr Val Val Pro Ser Gly Leu Asp
130                 135                 140

Ile Pro Asp Asp Pro Ala Gly Asp Cys Asp Pro Ser Leu His Val Leu
145                 150                 155                 160

Leu Arg Pro Thr Leu Leu Pro Lys Leu Leu Val Arg Ala Pro Phe Lys
            165                 170                 175

Ser Gly Ala Ala Ala Lys Tyr Ala Ala Val Ala Gly Leu Arg
            180                 185                 190

Asp Ala Ala His Arg Leu Gln Gln Tyr Met Phe Phe Met Arg Pro Ala
            195                 200                 205

Asp Pro Ser Arg Pro Ser Thr Asp Thr Ala Leu Arg Leu Ser Glu Leu
            210                 215                 220

Leu Ala Tyr Val Ser Val Leu Tyr His Trp Ala Ser Trp Met Leu Trp
225                 230                 235                 240

Thr Ala Asp Lys Tyr Val Cys Arg Arg Leu Gly Pro Ala Asp Arg Arg
            245                 250                 255

Phe Val Ala Leu Ser Gly Ser Leu Glu Ala Pro Ala Glu Thr Phe Ala
            260                 265                 270

Arg His Leu Asp Arg Gly Pro Ser Gly Thr Thr Gly Ser Met Gln Cys
            275                 280                 285

Met Ala Leu Arg Ala Ala Val Ser Asp Val Leu Gly His Leu Thr Arg
            290                 295                 300

Leu Ala His Leu Trp Glu Thr Gly Lys Arg Ser Gly Gly Thr Tyr Gly
305                 310                 315                 320

Ile Val Asp Ala Ile Val Ser Thr Val Glu Val Leu Ser Ile Val His
            325                 330                 335

His His Ala Gln Tyr Ile Ile Asn Ala Thr Leu Thr Gly Tyr Val Val
            340                 345                 350

Trp Ala Ser Asp Ser Leu Asn Asn Glu Tyr Leu Thr Ala Ala Val Asp
            355                 360                 365

Ser Gln Glu Arg Phe Cys Arg Thr Ala Ala Pro Leu Phe Pro Thr Met
            370                 375                 380

Thr Ala Pro Ser Trp Ala Arg Met Glu Leu Ser Ile Lys Ser Trp Phe
385                 390                 395                 400

Gly Ala Ala Leu Ala Pro Asp Leu Leu Arg Ser Gly Thr Pro Ser Pro
            405                 410                 415

His Tyr Glu Ser Ile Leu Arg Leu Ala Ala Ser Gly Pro Pro Gly Gly
```

-continued

```
                420                 425                 430
Arg Gly Ala Val Gly Gly Ser Cys Arg Asp Lys Ile Gln Arg Thr Arg
            435                 440                 445

Arg Asp Asn Ala Pro Pro Leu Pro Arg Ala Arg Pro His Ser Thr
450                 455                 460

Pro Ala Ala Pro Arg Arg Cys Arg Arg His Arg Glu Asp Leu Pro Glu
465                 470                 475                 480

Pro Pro His Val Asp Ala Asp Arg Gly Pro Glu Pro Cys Ala Gly
                485                 490                 495

Arg Pro Ala Thr Tyr Tyr Thr His Met Ala Gly Ala Pro Pro Arg Leu
            500                 505                 510

Pro Pro Arg Asn Pro Ala Pro Pro Glu Gln Arg Pro Ala Ala Ala
            515                 520                 525

Arg Pro Leu Ala Ala Gln Arg Glu Ala Ala Gly Val Tyr Asp Ala Val
            530                 535                 540

Arg Thr Trp Gly Pro Asp Ala Glu Ala Glu Pro Asp Gln Met Glu Asn
545                 550                 555                 560

Thr Tyr Leu Leu Pro Asp Asp Ala Ala Met Pro Ala Gly Val Gly
                565                 570                 575

Leu Gly Ala Thr Pro Ala Ala Asp Thr Thr Ala Ala Ala Trp Pro
            580                 585                 590

Ala Glu Ser His Ala Pro Arg Ala Pro Ser Glu Asp Ala Asp Ser Ile
            595                 600                 605

Tyr Glu Ser Val Gly Glu Asp Gly Gly Arg Val Tyr Glu Glu Ile Pro
            610                 615                 620

Trp Val Arg Val Tyr Glu Asn Ile Cys Pro Arg Arg Arg Leu Ala Gly
625                 630                 635                 640

Gly Ala Ala Leu Pro Gly Asp Ala Pro Asp Ser Pro Tyr Ile Glu Ala
                645                 650                 655

Glu Asn Pro Leu Tyr Asp Trp Gly Gly Ser Ala Leu Phe Ser Pro Arg
            660                 665                 670

Arg Ala Thr Arg Ala Pro Asp Pro Gly Leu Ser Leu Ser Pro Met Pro
            675                 680                 685

Ala Arg Pro Arg Thr Asn Ala Leu Ala Asn Asp Gly Pro Thr Asn Val
690                 695                 700

Ala Ala Leu Ser Ala Leu Leu Thr Lys Leu Lys Arg Gly Arg His Gln
705                 710                 715                 720

Ser His
```

<210> SEQ ID NO 8
<211> LENGTH: 300
<212> TYPE: PRT
<213> ORGANISM: herpes simplex virus 2

<400> SEQUENCE: 8

```
Met Thr Ser Arg Arg Ser Val Lys Ser Cys Pro Arg Glu Ala Pro Arg
1               5                   10                  15

Gly Thr His Glu Glu Leu Tyr Tyr Gly Pro Val Ser Pro Ala Asp Pro
            20                  25                  30

Glu Ser Pro Arg Asp Asp Phe Arg Arg Gly Ala Gly Pro Met Arg Ala
        35                  40                  45

Arg Pro Arg Gly Glu Val Arg Phe Leu His Tyr Asp Glu Ala Gly Tyr
    50                  55                  60

Ala Leu Tyr Arg Asp Ser Ser Ser Asp Asp Asp Glu Ser Arg Asp Thr
```

```
                65                  70                  75                  80
Ala Arg Pro Arg Ser Ala Ser Val Ala Gly Ser His Gly Pro Gly
                    85                  90                  95

Pro Ala Arg Ala Pro Pro Gly Gly Pro Val Gly Ala Gly Gly
            100                 105                 110

Arg Ser His Ala Pro Pro Ala Thr Pro Lys Met Thr Arg Gly Ala
            115                 120                 125

Pro Lys Ala Ser Ala Thr Pro Ala Thr Asp Pro Ala Arg Gly Arg
130                 135                 140

Pro Ala Gln Ala Asp Ser Ala Val Leu Leu Asp Ala Pro Ala Pro Thr
145                 150                 155                 160

Ala Ser Gly Arg Thr Lys Thr Pro Ala Gln Gly Leu Ala Lys Lys Leu
                165                 170                 175

His Phe Ser Thr Ala Pro Pro Ser Pro Thr Ala Pro Trp Thr Pro Arg
            180                 185                 190

Val Ala Gly Phe Asn Lys Arg Val Phe Cys Ala Ala Val Gly Arg Leu
            195                 200                 205

Ala Ala Thr His Ala Arg Leu Ala Ala Val Gln Leu Trp Asp Met Ser
210                 215                 220

Arg Pro His Thr Asp Glu Asp Leu Asn Glu Leu Leu Asp Leu Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Ala Ala Gln Asp Val Asp Ala Thr Ala Ala
            260                 265                 270

Ala Arg Gly Arg Pro Ala Gly Arg Ala Ala Thr Ala Arg Ala Pro
            275                 280                 285

Ala Arg Ser Ala Ser Arg Pro Arg Pro Leu Glu
            290                 295                 300

<210> SEQ ID NO 9
<211> LENGTH: 825
<212> TYPE: PRT
<213> ORGANISM: herpes simplex virus 2

<400> SEQUENCE: 9

Met Glu Pro Arg Pro Gly Thr Ser Arg Ala Asp Pro Gly Pro Glu
1               5                   10                  15

Arg Pro Pro Arg Gln Thr Pro Gly Thr Gln Pro Ala Ala Pro His Ala
                20                  25                  30

Trp Gly Met Leu Asn Asp Met Gln Trp Leu Ala Ser Asp Ser Glu
            35                  40                  45

Glu Glu Thr Glu Val Gly Ile Ser Asp Asp Leu His Arg Asp Ser
50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Ala Glu Arg Gln Gly
                85                  90                  95

Ser Pro Thr Pro Ala Asp Ala Gln Gly Ser Cys Gly Gly Pro Val
            100                 105                 110

Gly Glu Glu Glu Ala Glu Ala Gly Gly Gly Asp Val Cys Ala Val
            115                 120                 125

Cys Thr Asp Glu Ile Ala Pro Pro Leu Arg Cys Gln Ser Phe Pro Cys
            130                 135                 140
```

```
Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
            165                 170                 175

Val Thr Ala Ser Gly Ser Phe Ser Thr Ile Pro Ile Val Asn Asp Pro
            180                 185                 190

Arg Thr Arg Val Glu Ala Glu Ala Val Arg Ala Gly Thr Ala Val
            195                 200                 205

Asp Phe Ile Trp Thr Gly Asn Pro Arg Thr Ala Pro Arg Ser Leu Ser
    210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Ala Gly Ala
                260                 265                 270

Thr Arg Gly Thr Ser Gln Pro Ala Ala Thr Arg Pro Ala Pro Pro Gly
            275                 280                 285

Ala Pro Arg Ser Ser Ser Gly Gly Ala Pro Leu Arg Ala Gly Val
    290                 295                 300

Gly Ser Gly Ser Gly Gly Pro Ala Val Ala Ala Val Val Pro Arg
305                 310                 315                 320

Val Ala Ser Leu Pro Pro Ala Ala Gly Gly Arg Ala Gln Ala Arg
                325                 330                 335

Arg Val Gly Glu Asp Ala Ala Ala Glu Gly Arg Thr Pro Pro Ala
            340                 345                 350

Arg Gln Pro Arg Ala Ala Gln Glu Pro Pro Ile Val Ile Ser Asp Ser
            355                 360                 365

Pro Pro Pro Ser Pro Arg Arg Pro Ala Gly Pro Gly Pro Leu Ser Phe
    370                 375                 380

Val Ser Ser Ser Ser Ala Gln Val Ser Ser Gly Pro Gly Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Pro Val Val Ser
            420                 425                 430

Ala Ser Ala Asp Ala Ala Gly Pro Ala Pro Pro Ala Val Pro Val Asp
                435                 440                 445

Ala His Arg Ala Pro Arg Ser Arg Met Thr Gln Ala Gln Thr Asp Thr
    450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
                485                 490                 495

Thr Pro Gly Ala Ala Pro His Ala Ala Glu Gly Ala Ala Ala Arg Pro
            500                 505                 510

Arg Lys Arg Arg Gly Ser Asp Ser Gly Pro Ala Ala Ser Ser Ser Ala
        515                 520                 525

Ser Ser Ser Ala Ala Pro Arg Ser Pro Leu Ala Pro Gln Gly Val Gly
            530                 535                 540

Ala Lys Arg Ala Ala Pro Arg Arg Ala Pro Asp Ser Asp Ser Gly Asp
545                 550                 555                 560

Arg Gly His Gly Pro Leu Ala Pro Ala Ser Ala Gly Ala Ala Pro Pro
```

```
                    565                 570                 575

Ser Ala Ser Pro Ser Gln Ala Ala Val Ala Ala Ser Ser Ser
            580                 585                 590

Ser Ala Ser Ser Ser Ala Ser Ser Ser Ala Ser Ser Ser Ser
        595                 600                 605

Ala Ser Ser Ser Ala Ser Ser Ser Ala Ser Ser Ser Ala
    610                 615                 620

Ser Ser Ser Ala Gly Gly Ala Gly Ser Val Ala Ser Ala Ser Gly
625                 630                 635                 640

Ala Gly Glu Arg Arg Glu Thr Ser Leu Gly Pro Arg Ala Ala Pro
                645                 650                 655

Arg Gly Pro Arg Lys Cys Ala Arg Lys Thr Arg His Ala Glu Gly Gly
            660                 665                 670

Pro Glu Pro Gly Ala Arg Asp Pro Ala Pro Gly Leu Thr Arg Tyr Leu
        675                 680                 685

Pro Ile Ala Gly Val Ser Val Val Ala Leu Ala Pro Tyr Val Asn
    690                 695                 700

Lys Thr Val Thr Gly Asp Cys Leu Pro Val Leu Asp Met Glu Thr Gly
705                 710                 715                 720

His Ile Gly Ala Tyr Val Leu Val Asp Gln Thr Gly Asn Val Ala
                725                 730                 735

Asp Leu Leu Arg Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
    770                 775                 780

Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
                805                 810                 815

Gly Asp Ala Pro Ala Gly His Gly Glu
            820                 825

<210> SEQ ID NO 10
<211> LENGTH: 1196
<212> TYPE: PRT
<213> ORGANISM: herpes simplex virus 2

<400> SEQUENCE: 10

Met Asp Thr Lys Pro Lys Thr Thr Thr Thr Val Lys Val Pro Pro Gly
1               5                   10                  15

Pro Met Gly Tyr Val Tyr Gly Arg Ala Cys Pro Ala Glu Gly Leu Glu
            20                  25                  30

Leu Leu Ser Leu Leu Ser Ala Arg Ser Gly Asp Ala Asp Val Ala Val
        35                  40                  45

Ala Pro Leu Ile Val Gly Leu Thr Val Glu Ser Gly Phe Glu Ala Asn
    50                  55                  60

Val Ala Ala Val Val Gly Ser Arg Thr Gly Leu Gly Gly Thr Ala
65                  70                  75                  80

Val Ser Leu Lys Leu Met Pro Ser His Tyr Ser Pro Ser Val Tyr Val
                85                  90                  95

Phe His Gly Gly Arg His Leu Ala Pro Ser Thr Gln Ala Pro Asn Leu
            100                 105                 110
```

```
Thr Arg Leu Cys Glu Arg Ala Arg Pro His Phe Gly Phe Ala Asp Tyr
            115                 120                 125

Ala Pro Arg Pro Cys Asp Leu Lys His Glu Thr Thr Gly Asp Ala Leu
    130                 135                 140

Cys Glu Arg Leu Gly Leu Asp Pro Asp Arg Ala Leu Leu Tyr Leu Val
145                 150                 155                 160

Ile Thr Glu Gly Phe Arg Glu Ala Val Cys Ile Ser Asn Thr Phe Leu
                165                 170                 175

His Leu Gly Gly Met Asp Lys Val Thr Ile Gly Asp Ala Glu Val His
            180                 185                 190

Arg Ile Pro Val Tyr Pro Leu Gln Met Phe Met Pro Asp Phe Ser Arg
        195                 200                 205

Val Ile Ala Asp Pro Phe Asn Cys Asn His Arg Ser Ile Gly Glu Asn
    210                 215                 220

Phe Asn Tyr Pro Leu Pro Phe Phe Asn Arg Pro Leu Ala Arg Leu Leu
225                 230                 235                 240

Phe Glu Ala Val Val Gly Pro Ala Ala Val Ala Leu Arg Ala Arg Asn
                245                 250                 255

Val Asp Ala Val Ala Arg Ala Ala His Leu Ala Phe Asp Glu Asn
            260                 265                 270

His Glu Gly Ala Ala Leu Pro Ala Asp Ile Thr Phe Thr Ala Phe Glu
        275                 280                 285

Ala Ser Gln Gly Lys Pro Gln Arg Gly Ala Arg Asp Ala Gly Asn Lys
    290                 295                 300

Gly Pro Ala Gly Gly Phe Glu Gln Arg Leu Ala Ser Val Met Ala Gly
305                 310                 315                 320

Asp Ala Ala Leu Ala Leu Glu Ser Ile Val Ser Met Ala Val Phe Asp
                325                 330                 335

Glu Pro Pro Pro Asp Ile Thr Thr Trp Pro Leu Leu Glu Gly Gln Glu
            340                 345                 350

Thr Pro Ala Ala Arg Ala Gly Ala Val Gly Ala Tyr Leu Ala Arg Ala
        355                 360                 365

Ala Gly Leu Val Gly Ala Met Val Phe Ser Thr Asn Ser Ala Leu His
    370                 375                 380

Leu Thr Glu Val Asp Asp Ala Gly Pro Ala Asp Pro Lys Asp His Ser
385                 390                 395                 400

Lys Pro Ser Phe Tyr Arg Phe Phe Leu Val Pro Gly Thr His Val Ala
                405                 410                 415

Ala Asn Pro Gln Leu Asp Arg Glu Gly His Val Val Pro Gly Tyr Glu
            420                 425                 430

Gly Arg Pro Thr Ala Pro Leu Val Gly Gly Thr Gln Glu Phe Ala Gly
        435                 440                 445

Glu His Leu Ala Met Leu Cys Gly Phe Ser Pro Ala Leu Leu Ala Lys
    450                 455                 460

Met Leu Phe Tyr Leu Glu Arg Cys Asp Gly Gly Val Ile Val Gly Arg
465                 470                 475                 480

Gln Glu Met Asp Val Phe Arg Tyr Val Ala Asp Ser Gly Gln Thr Asp
                485                 490                 495

Val Pro Cys Asn Leu Cys Thr Phe Glu Thr Arg His Ala Cys Ala His
            500                 505                 510

Thr Thr Leu Met Arg Leu Arg Ala Arg His Pro Lys Phe Ala Ser Ala
        515                 520                 525

Ala Arg Gly Ala Ile Gly Val Phe Gly Thr Met Asn Ser Ala Tyr Ser
```

-continued

```
              530                 535                 540
Asp Cys Asp Val Leu Gly Asn Tyr Ala Ala Phe Ser Ala Leu Lys Arg
545                 550                 555                 560

Ala Asp Gly Ser Glu Asn Thr Arg Thr Ile Met Gln Glu Thr Tyr Arg
                565                 570                 575

Ala Ala Thr Glu Arg Val Met Ala Glu Leu Glu Ala Leu Gln Tyr Val
            580                 585                 590

Asp Gln Ala Val Pro Thr Ala Leu Gly Arg Leu Glu Thr Ile Ile Gly
        595                 600                 605

Asn Arg Glu Ala Leu His Thr Val Val Asn Asn Ile Lys Gln Leu Val
    610                 615                 620

Asp Arg Glu Val Glu Gln Leu Met Arg Asn Leu Ile Glu Gly Arg Asn
625                 630                 635                 640

Phe Lys Phe Arg Asp Gly Leu Ala Glu Ala Asn His Ala Met Ser Leu
                645                 650                 655

Ser Leu Asp Pro Tyr Thr Cys Gly Pro Cys Pro Leu Leu Gln Leu Leu
            660                 665                 670

Ala Arg Arg Ser Asn Leu Ala Val Tyr Gln Asp Leu Ala Leu Ser Gln
        675                 680                 685

Cys His Gly Val Phe Ala Gly Gln Ser Val Glu Gly Arg Asn Phe Arg
    690                 695                 700

Asn Gln Phe Gln Pro Val Leu Arg Arg Val Met Asp Leu Phe Asn
705                 710                 715                 720

Asn Gly Phe Leu Ser Ala Lys Thr Leu Thr Val Ala Leu Ser Glu Gly
                725                 730                 735

Ala Ala Ile Cys Ala Pro Ser Leu Thr Ala Gly Gln Thr Ala Pro Ala
            740                 745                 750

Glu Ser Ser Phe Glu Gly Asp Val Ala Arg Val Thr Leu Gly Phe Pro
        755                 760                 765

Lys Glu Leu Arg Val Lys Ser Arg Val Leu Phe Ala Gly Ala Ser Ala
    770                 775                 780

Asn Ala Ser Glu Ala Ala Lys Ala Arg Val Ala Ser Leu Gln Ser Ala
785                 790                 795                 800

Tyr Gln Lys Pro Asp Lys Arg Val Asp Ile Leu Leu Gly Pro Leu Gly
                805                 810                 815

Phe Leu Leu Lys Gln Phe His Ala Val Ile Phe Pro Asn Gly Lys Pro
            820                 825                 830

Pro Gly Ser Asn Gln Pro Asn Pro Gln Trp Phe Trp Thr Ala Leu Gln
        835                 840                 845

Arg Asn Gln Leu Pro Ala Arg Leu Leu Ser Arg Glu Asp Ile Glu Thr
    850                 855                 860

Ile Ala Phe Ile Lys Arg Phe Ser Leu Asp Tyr Gly Ala Ile Asn Phe
865                 870                 875                 880

Ile Asn Leu Ala Pro Asn Asn Val Ser Glu Leu Ala Met Tyr Tyr Met
                885                 890                 895

Ala Asn Gln Ile Leu Arg Tyr Cys Asp His Ser Thr Tyr Phe Ile Asn
            900                 905                 910

Thr Leu Thr Ala Val Ile Ala Gly Ser Arg Arg Pro Pro Ser Val Gln
        915                 920                 925

Ala Ala Ala Ala Trp Ala Pro Gln Gly Gly Ala Gly Leu Glu Ala Gly
    930                 935                 940

Ala Arg Ala Leu Met Asp Ser Leu Asp Ala His Pro Gly Ala Trp Thr
945                 950                 955                 960
```

```
Ser Met Phe Ala Ser Cys Asn Leu Leu Arg Pro Val Met Ala Ala Arg
            965                 970                 975

Pro Met Val Val Leu Gly Leu Ser Ile Ser Lys Tyr Tyr Gly Met Ala
            980                 985                 990

Gly Asn Asp Arg Val Phe Gln Ala Gly Asn Trp Ala Ser Leu Leu Gly
        995                 1000                1005

Gly Lys Asn Ala Cys Pro Leu Leu Ile Phe Asp Arg Thr Arg Lys
    1010                1015                1020

Phe Val Leu Ala Cys Pro Arg Ala Gly Phe Val Cys Ala Ala Ser
    1025                1030                1035

Ser Leu Gly Gly Gly Ala His Glu His Ser Leu Cys Glu Gln Leu
    1040                1045                1050

Arg Gly Ile Ile Ala Glu Gly Gly Ala Ala Val Ala Ser Ser Val
    1055                1060                1065

Phe Val Ala Thr Val Lys Ser Leu Gly Pro Arg Thr Gln Gln Leu
    1070                1075                1080

Gln Ile Glu Asp Trp Leu Ala Leu Leu Glu Asp Glu Tyr Leu Ser
    1085                1090                1095

Glu Glu Met Met Glu Phe Thr Thr Arg Ala Leu Glu Arg Gly His
    1100                1105                1110

Gly Glu Trp Ser Thr Asp Ala Ala Leu Glu Val Ala His Glu Ala
    1115                1120                1125

Glu Ala Leu Val Ser Gln Leu Gly Ala Ala Gly Glu Val Phe Asn
    1130                1135                1140

Phe Gly Asp Phe Gly Asp Glu Asp Asp His Ala Ala Ser Phe Gly
    1145                1150                1155

Gly Leu Ala Ala Ala Ala Gly Ala Ala Gly Val Ala Arg Lys Arg
    1160                1165                1170

Ala Phe His Gly Asp Asp Pro Phe Gly Glu Gly Pro Pro Glu Lys
    1175                1180                1185

Lys Asp Leu Thr Leu Asp Met Leu
    1190                1195

<210> SEQ ID NO 11
<211> LENGTH: 1142
<212> TYPE: PRT
<213> ORGANISM: herpes simplex virus 2

<400> SEQUENCE: 11

Met Ala Asn Arg Pro Ala Ala Ser Ala Leu Ala Gly Ala Arg Ser Pro
1               5                   10                  15

Ser Glu Arg Gln Glu Pro Arg Glu Pro Glu Val Ala Pro Pro Gly Gly
            20                  25                  30

Asp His Val Phe Cys Arg Lys Val Ser Gly Val Met Val Leu Ser Ser
        35                  40                  45

Asp Pro Pro Gly Pro Ala Ala Tyr Arg Ile Ser Asp Ser Ser Phe Val
    50                  55                  60

Gln Cys Gly Ser Asn Cys Ser Met Ile Ile Asp Gly Asp Val Ala Arg
65                  70                  75                  80

Gly His Leu Arg Asp Leu Glu Ala Thr Ser Thr Gly Ala Phe Val
            85                  90                  95

Ala Ile Ser Asn Val Ala Ala Gly Gly Asp Gly Arg Thr Ala Val Val
            100                 105                 110

Ala Leu Gly Gly Thr Ser Gly Pro Ser Ala Thr Thr Ser Val Gly Thr
```

```
            115                 120                 125
Gln Thr Ser Gly Glu Phe Leu His Gly Asn Pro Arg Thr Pro Glu Pro
130                 135                 140

Gln Gly Pro Gln Ala Val Pro Pro Pro Pro Pro Pro Phe Pro Trp
145                 150                 155                 160

Gly His Glu Cys Cys Ala Arg Arg Asp Ala Arg Gly Gly Ala Glu Lys
                165                 170                 175

Asp Val Gly Ala Ala Glu Ser Trp Ser Asp Gly Pro Ser Ser Asp Ser
                180                 185                 190

Glu Thr Glu Asp Ser Asp Ser Asp Glu Asp Thr Gly Ser Glu Thr
                195                 200                 205

Leu Ser Arg Ser Ser Ser Ile Trp Ala Ala Gly Ala Thr Asp Asp Asp
210                 215                 220

Asp Ser Asp Ser Asp Ser Arg Ser Asp Asp Ser Val Gln Pro Asp Val
225                 230                 235                 240

Val Val Arg Arg Arg Trp Ser Asp Gly Pro Ala Pro Val Ala Phe Pro
                245                 250                 255

Lys Pro Arg Arg Pro Gly Asp Ser Pro Gly Asn Pro Gly Leu Gly Ala
                260                 265                 270

Gly Thr Gly Pro Gly Ser Ala Thr Asp Pro Arg Ala Ser Ala Asp Ser
                275                 280                 285

Asp Ser Ala Ala His Ala Ala Ala Pro Gln Ala Asp Val Ala Pro Val
                290                 295                 300

Leu Asp Ser Gln Pro Thr Val Gly Thr Asp Pro Gly Tyr Pro Val Pro
305                 310                 315                 320

Leu Glu Leu Thr Pro Glu Asn Ala Glu Ala Val Ala Arg Phe Leu Gly
                325                 330                 335

Asp Ala Val Asp Arg Glu Pro Ala Leu Met Leu Glu Tyr Phe Cys Arg
                340                 345                 350

Cys Ala Arg Glu Glu Ser Lys Arg Val Pro Pro Arg Thr Phe Gly Ser
                355                 360                 365

Ala Pro Arg Leu Thr Glu Asp Asp Phe Gly Leu Leu Asn Tyr Ala Leu
                370                 375                 380

Ala Glu Met Arg Arg Leu Cys Leu Asp Leu Pro Pro Val Pro Pro Asn
385                 390                 395                 400

Ala Tyr Thr Pro Tyr His Leu Arg Glu Tyr Ala Thr Arg Leu Val Asn
                405                 410                 415

Gly Phe Lys Pro Leu Val Arg Arg Ser Ala Arg Leu Tyr Arg Ile Leu
                420                 425                 430

Gly Val Leu Val His Leu Arg Ile Arg Thr Arg Glu Ala Ser Phe Glu
                435                 440                 445

Glu Trp Met Arg Ser Lys Glu Val Asp Leu Asp Phe Gly Leu Thr Glu
                450                 455                 460

Arg Leu Arg Glu His Glu Ala Gln Leu Met Ile Leu Ala Gln Ala Leu
465                 470                 475                 480

Asn Pro Tyr Asp Cys Leu Ile His Ser Thr Pro Asn Thr Leu Val Glu
                485                 490                 495

Arg Gly Leu Gln Ser Ala Leu Lys Tyr Glu Glu Phe Tyr Leu Lys Arg
                500                 505                 510

Phe Gly Gly His Tyr Met Glu Ser Val Phe Gln Met Tyr Thr Arg Ile
                515                 520                 525

Ala Gly Phe Leu Ala Cys Arg Ala Thr Arg Gly Met Arg His Ile Ala
                530                 535                 540
```

-continued

Leu Gly Arg Gln Gly Ser Trp Trp Glu Met Phe Lys Phe Phe His
545                 550                 555                 560

Arg Leu Tyr Asp His Gln Ile Val Pro Ser Thr Pro Ala Met Leu Asn
                565                 570                 575

Leu Gly Thr Arg Asn Tyr Tyr Thr Ser Ser Cys Tyr Leu Val Asn Pro
            580                 585                 590

Gln Ala Thr Thr Asn Gln Ala Thr Leu Arg Ala Ile Thr Gly Asn Val
        595                 600                 605

Ser Ala Ile Leu Ala Arg Asn Gly Gly Ile Gly Leu Cys Met Gln Ala
610                 615                 620

Phe Asn Asp Ala Ser Pro Gly Thr Ala Ser Ile Met Pro Ala Leu Lys
625                 630                 635                 640

Val Leu Asp Ser Leu Val Ala Ala His Asn Lys Gln Ser Thr Arg Pro
                645                 650                 655

Thr Gly Ala Cys Val Tyr Leu Glu Pro Trp His Ser Asp Val Arg Ala
            660                 665                 670

Val Leu Arg Met Lys Gly Val Leu Ala Gly Glu Ala Gln Arg Cys
        675                 680                 685

Asp Asn Ile Phe Ser Ala Leu Trp Met Pro Asp Leu Phe Phe Lys Arg
690                 695                 700

Leu Ile Arg His Leu Asp Gly Glu Lys Asn Val Thr Trp Ser Leu Phe
705                 710                 715                 720

Asp Arg Asp Thr Ser Met Ser Leu Ala Asp Phe His Gly Glu Glu Phe
                725                 730                 735

Glu Lys Leu Tyr Glu His Leu Glu Ala Met Gly Phe Gly Glu Thr Ile
            740                 745                 750

Pro Ile Gln Asp Leu Ala Tyr Ala Ile Val Arg Ser Ala Ala Thr Thr
        755                 760                 765

Gly Ser Pro Phe Ile Met Phe Lys Asp Ala Val Asn Arg His Tyr Ile
770                 775                 780

Tyr Asp Thr Gln Gly Ala Ala Ile Ala Gly Ser Asn Leu Cys Thr Glu
785                 790                 795                 800

Ile Val His Pro Ala Ser Lys Arg Ser Ser Gly Val Cys Asn Leu Gly
                805                 810                 815

Ser Val Asn Leu Ala Arg Cys Val Ser Arg Gln Thr Phe Asp Phe Gly
            820                 825                 830

Arg Leu Arg Asp Ala Val Gln Ala Cys Val Leu Met Val Asn Ile Met
        835                 840                 845

Ile Asp Ser Thr Leu Gln Pro Thr Pro Gln Cys Thr Arg Gly Asn Asp
850                 855                 860

Asn Leu Arg Ser Met Gly Ile Gly Met Gln Gly Leu His Thr Ala Cys
865                 870                 875                 880

Leu Lys Met Gly Leu Asp Leu Glu Ser Ala Glu Phe Arg Asp Leu Asn
                885                 890                 895

Thr His Ile Ala Glu Val Met Leu Leu Ala Ala Met Lys Thr Ser Asn
            900                 905                 910

Ala Leu Cys Val Arg Gly Ala Arg Pro Phe Ser His Phe Lys Arg Ser
        915                 920                 925

Met Tyr Arg Ala Gly Arg Phe His Trp Glu Arg Phe Ser Asn Ala Ser
930                 935                 940

Pro Arg Tyr Glu Gly Glu Trp Glu Met Leu Arg Gln Ser Met Met Lys
945                 950                 955                 960

His Gly Leu Arg Asn Ser Gln Phe Ile Ala Leu Met Pro Thr Ala Ala
            965                 970                 975

Ser Ala Gln Ile Ser Asp Val Ser Glu Gly Phe Ala Pro Leu Phe Thr
        980                 985                 990

Asn Leu Phe Ser Lys Val Thr Arg Asp Gly Glu Thr Leu Arg Pro Asn
    995                1000                1005

Thr Leu Leu Leu Lys Glu Leu Glu Arg Thr Phe Gly Gly Lys Arg
   1010                1015                1020

Leu Leu Asp Ala Met Asp Gly Leu Glu Ala Lys Gln Trp Ser Val
   1025                1030                1035

Ala Gln Ala Leu Pro Cys Leu Asp Pro Ala His Pro Leu Arg Arg
   1040                1045                1050

Phe Lys Thr Ala Phe Asp Tyr Asp Gln Glu Leu Leu Ile Asp Leu
   1055                1060                1065

Cys Ala Asp Arg Ala Pro Tyr Val Asp His Ser Gln Ser Met Thr
   1070                1075                1080

Leu Tyr Val Thr Glu Lys Ala Asp Gly Thr Leu Pro Ala Ser Thr
   1085                1090                1095

Leu Val Arg Leu Leu Val His Ala Tyr Lys Arg Gly Leu Lys Thr
   1100                1105                1110

Gly Met Tyr Tyr Cys Lys Val Arg Lys Ala Thr Asn Ser Gly Val
   1115                1120                1125

Phe Ala Gly Asp Asp Asn Ile Val Cys Thr Ser Cys Ala Leu
   1130                1135                1140

<210> SEQ ID NO 12
<211> LENGTH: 15
<212> TYPE: PRT
<213> ORGANISM: herpes simplex virus 2

<400> SEQUENCE: 12

Ala Phe Glu Asp Arg Ser Tyr Pro Ala Val Phe Tyr Leu Leu Gln
1               5                   10                  15

<210> SEQ ID NO 13
<211> LENGTH: 15
<212> TYPE: PRT
<213> ORGANISM: herpes simplex virus 2

<400> SEQUENCE: 13

Arg Leu Gly Pro Ala Asp Arg Arg Phe Val Ala Leu Ser Gly Ser
1               5                   10                  15

<210> SEQ ID NO 14
<211> LENGTH: 15
<212> TYPE: PRT
<213> ORGANISM: herpes simplex virus 2

<400> SEQUENCE: 14

Ala Gln Arg Glu Ala Ala Gly Val Tyr Asp Ala Val Arg Thr Trp
1               5                   10                  15

<210> SEQ ID NO 15
<211> LENGTH: 15
<212> TYPE: PRT
<213> ORGANISM: herpes simplex virus 2

<400> SEQUENCE: 15

Pro Met Arg Ala Arg Pro Arg Gly Glu Val Arg Phe Leu His Tyr
1               5                   10                  15

```
<210> SEQ ID NO 16
<211> LENGTH: 16
<212> TYPE: PRT
<213> ORGANISM: herpes simplex virus 2

<400> SEQUENCE: 16

Ala Arg Pro Arg Arg Ser Ala Ser Val Ala Gly Ser His Gly Pro Gly
1               5                   10                  15

<210> SEQ ID NO 17
<211> LENGTH: 16
<212> TYPE: PRT
<213> ORGANISM: herpes simplex virus 2

<400> SEQUENCE: 17

His Gly Pro Gly Pro Ala Arg Ala Pro Pro Pro Gly Gly Pro Val
1               5                   10                  15

<210> SEQ ID NO 18
<211> LENGTH: 15
<212> TYPE: PRT
<213> ORGANISM: herpes simplex virus 2

<400> SEQUENCE: 18

Pro Lys Ala Ser Ala Thr Pro Ala Thr Asp Pro Ala Arg Gly Arg
1               5                   10                  15

<210> SEQ ID NO 19
<211> LENGTH: 15
<212> TYPE: PRT
<213> ORGANISM: herpes simplex virus 2

<400> SEQUENCE: 19

Lys Asn Leu Leu Gln Arg Ala Asn Glu Leu Val Asn Pro Asp Ala
1               5                   10                  15

<210> SEQ ID NO 20
<211> LENGTH: 16
<212> TYPE: PRT
<213> ORGANISM: herpes simplex virus 2

<400> SEQUENCE: 20

Glu Ala Gly Leu Met Asp Ala Ala Thr Pro Pro Ala Arg Pro Pro Ala
1               5                   10                  15

<210> SEQ ID NO 21
<211> LENGTH: 15
<212> TYPE: PRT
<213> ORGANISM: herpes simplex virus 2

<400> SEQUENCE: 21

Leu His Pro Phe Cys Ile Pro Cys Met Lys Thr Trp Ile Pro Leu
1               5                   10                  15

<210> SEQ ID NO 22
<211> LENGTH: 15
<212> TYPE: PRT
<213> ORGANISM: herpes simplex virus 2

<400> SEQUENCE: 22

Asp Phe Ile Trp Thr Gly Asn Pro Arg Thr Ala Pro Arg Ser Leu
1               5                   10                  15
```

```
<210> SEQ ID NO 23
<211> LENGTH: 15
<212> TYPE: PRT
<213> ORGANISM: herpes simplex virus 7

<400> SEQUENCE: 23

Leu Pro Ile Ala Gly Val Ser Ser Val Val Ala Leu Ala Pro Tyr
1               5                   10                  15

<210> SEQ ID NO 24
<211> LENGTH: 15
<212> TYPE: PRT
<213> ORGANISM: herpes simplex virus 2

<400> SEQUENCE: 24

Asp Met Glu Thr Gly His Ile Gly Ala Tyr Val Val Leu Val Asp
1               5                   10                  15

<210> SEQ ID NO 25
<211> LENGTH: 15
<212> TYPE: PRT
<213> ORGANISM: herpes simplex virus 2

<400> SEQUENCE: 25

Gly His Ile Gly Ala Tyr Val Val Leu Val Asp Gln Thr Gly Asn
1               5                   10                  15

<210> SEQ ID NO 26
<211> LENGTH: 15
<212> TYPE: PRT
<213> ORGANISM: herpes simplex virus 2

<400> SEQUENCE: 26

Arg Ala Ala Ala Pro Ala Trp Ser Arg Arg Thr Leu Leu Pro Glu
1               5                   10                  15

<210> SEQ ID NO 27
<211> LENGTH: 15
<212> TYPE: PRT
<213> ORGANISM: herpes simplex virus 2

<400> SEQUENCE: 27

Pro Val Gly Asn Met Leu Phe Asp Gln Gly Thr Leu Val Gly Ala
1               5                   10                  15

<210> SEQ ID NO 28
<211> LENGTH: 15
<212> TYPE: PRT
<213> ORGANISM: herpes simplex virus 2

<400> SEQUENCE: 28

Leu Met Leu Glu Tyr Phe Cys Arg Cys Ala Arg Glu Glu Ser Lys
1               5                   10                  15

<210> SEQ ID NO 29
<211> LENGTH: 15
<212> TYPE: PRT
<213> ORGANISM: herpes simplex virus 2

<400> SEQUENCE: 29

Gly Val Leu Val His Leu Arg Ile Arg Thr Arg Glu Ala Ser Phe
1               5                   10                  15

<210> SEQ ID NO 30
<211> LENGTH: 15
```

```
<212> TYPE: PRT
<213> ORGANISM: herpes simplex virus 2

<400> SEQUENCE: 30

Phe Gly Gly His Tyr Met Glu Ser Val Phe Gln Met Tyr Thr Arg
1               5                   10                  15

<210> SEQ ID NO 31
<211> LENGTH: 15
<212> TYPE: PRT
<213> ORGANISM: herpes simplex virus 2

<400> SEQUENCE: 31

Ser Met Ser Leu Ala Asp Phe His Gly Glu Glu Phe Glu Lys Leu
1               5                   10                  15

<210> SEQ ID NO 32
<211> LENGTH: 15
<212> TYPE: PRT
<213> ORGANISM: herpes simplex virus 2

<400> SEQUENCE: 32

Lys Thr Ser Asn Ala Leu Cys Val Arg Gly Ala Arg Pro Phe Ser
1               5                   10                  15

<210> SEQ ID NO 33
<211> LENGTH: 15
<212> TYPE: PRT
<213> ORGANISM: herpes simplex virus 2

<400> SEQUENCE: 33

Cys Pro Leu Leu Ile Phe Asp Arg Thr Arg Lys Phe Val Leu Ala
1               5                   10                  15
```